United States Patent
Lind et al.

(10) Patent No.: US 11,555,222 B2
(45) Date of Patent: Jan. 17, 2023

(54) PCR CONTROLS

(71) Applicant: OSLO UNIVERSITETSSYKEHUS HF, Oslo (NO)

(72) Inventors: Guro E. Lind, Oslo (NO); Marine Jeanmougin, Oslo (NO); Heidi D. Pharo, Oslo (NO); Kim Andresen, Nesbru (NO); Ragnhild Lothe, Oslo (NO)

(73) Assignee: OSLO UNIVERSITETSSYKEHUS HF, Oslo (NO)

( * ) Notice: Subject to any disclaimer, the term of this patent is extended or adjusted under 35 U.S.C. 154(b) by 138 days.

(21) Appl. No.: 16/768,627

(22) PCT Filed: Nov. 30, 2018

(86) PCT No.: PCT/EP2018/083147
§ 371 (c)(1),
(2) Date: May 29, 2020

(87) PCT Pub. No.: WO2019/106149
PCT Pub. Date: Jun. 6, 2019

(65) Prior Publication Data
US 2021/0032701 A1 Feb. 4, 2021

(30) Foreign Application Priority Data
Dec. 1, 2017 (GB) .................................. 1720088

(51) Int. Cl.
*C12Q 1/6886* (2018.01)
*C12Q 1/686* (2018.01)

(52) U.S. Cl.
CPC .......... *C12Q 1/6886* (2013.01); *C12Q 1/686* (2013.01); *C12Q 2523/125* (2013.01); *C12Q 2545/114* (2013.01); *C12Q 2561/101* (2013.01); *C12Q 2563/107* (2013.01); *C12Q 2600/154* (2013.01); *C12Q 2600/166* (2013.01)

(58) Field of Classification Search
CPC .................... C12Q 1/686; C12Q 2545/114
See application file for complete search history.

(56) References Cited

U.S. PATENT DOCUMENTS

2003/0165832 A1   9/2003   Sagner et al.

FOREIGN PATENT DOCUMENTS

| WO | WO 03/070980 A2 | 8/2003 |
|----|----|----|
| WO | WO 2008/122097 A1 | 10/2008 |
| WO | WO 2014/178689 A1 | 11/2014 |

OTHER PUBLICATIONS

Ahmed, et al., "Epigenetic and genetic features of 24 colon cancer cell lines," Oncogenesis 2, e71, Sep. 16, 2013, 8 pages.
Attali, et al., "ddpcr: an R package and web application for analysis of droplet digital PCR data [version 1; referees: 2 approved]," F1000Research 2016, 5:1411, Sep. 14, 2016, 11 pages.
Berg et al., "Multi-omics of 34 colorectal cancer cell lines—a resource for biomedical studies," Molecular Cancer (2017) 16:116, 16 pages.
Cao, et al., "Advances in digital polymerase chain reaction (dPCR) and its emerging biomedical applications," Biosensors and Bioelectronics 90 (2017) 459-474, 16 pages.
Chiu, et al., "twoddpcr: an R/Bioconductor package and Shiny app for Droplet Digital PCR analysis," Bioinformatics, 1-3, May 5, 2017, 3 pages.
Eads, et al., "MethyLight: a high-throughput assay to measure DNA methylation," Nucleic Acids Research, vol. 28, No. 8, Jan. 25, 2000, 8 pages.
Gerdes, et al., "Optimization of digital droplet polymerase chain reaction for quantification of genetically modified organisms," Biomolecular Detection and Quantification 7 (2016) pp. 9-20.
Hindson, et al., "High-Throughput Droplet Digital PCR System for Absolute Quantitation of DNA Copy Number," Analytical Chemistry, 83, American Chemical Society, Oct. 28, 2011, pp. 8604-8610.
Huggett, et al., "QPCR, dPCR, NGS—A journey," Biomolecular Detection and Quantification 3, Jan. 15, 2015, pp. A1-A5.
Jeanmougin, et al., "DNA methylation using droplet digital PCR Estimation of a threshold for positive droplets quantification," Oslo University Hospital, 2017, 1 page.
Lu, et al., "High levels of EphA3 expression are associated with high invasive capacity and poor overall survival in hepatocellular carcinoma," Oncology Reports 30, Aug. 8, 2013, pp. 2179-2186.
Morley, et al., "Digital PCR: a brief history," Biomolecular Detection and Quantification 1 (2014) 1-2, Aug. 14, 2014, 3 pages.
Morrison, et al., "Nanoliter high throughput quantitative PCR," Nucleic Acids Research, vol. 34, No. 18, e123, Sep. 25, 2006, 9 pages.
Ottesen, et al., "Microfluidic Digital PCR Enables Multigene Analysis of Individual Environmental Bacteria," www.sciencemag.org, Science vol. 314, Dec. 1, 2006, 5 pages.
Park, et al., "Molecular evidence for two-stage learning and partial laterality in eyeblink conditioning of mice," PNAS, vol. 103, No. 14, Apr. 4, 2006, pp. 5549-5554.
Pavšič, et al., "Assessment of the real-time PCR and different digital PCR platforms for DNA quantification," Anal Bioanal Chem (2016) 408, Oct. 31, 2015, pp. 107-121.
Pekin, et al., "Quantitative and sensitive detection of rare mutations using droplet-based Microfluidics," Lab Chip, 11, Apr. 4, 2011, pp. 2156-2166.

(Continued)

Primary Examiner — Teresa E Strzelecka
(74) Attorney, Agent, or Firm — Lewis Roca Rothgerber Christie LLP

(57) ABSTRACT

The present invention provides a method of quantification of a target nucleic acid, using at least any two of the genes SYT10, EPHA3, PLEKHF1 and KBTBD4 as control genes. In particular, the combination of the genes SYT10, EPHA3, PLEKHF1 and KBTBD4, known as the 4Plex, is provided as a control for nucleic acid quantification. The 4Plex has particular utility as a control for nucleic acid quantification by methylation-specific droplet digital PCR.

21 Claims, 12 Drawing Sheets
(2 of 12 Drawing Sheet(s) Filed in Color)
Specification includes a Sequence Listing.

(56) References Cited

OTHER PUBLICATIONS

Pharo, et al., "Abstract 5387: Droplet digital PCR for sensitive quantification of DNA methylation in non-invasive material: Development of a robust control," Molecular and Cellular Biology, Genetics, Jul. 2017, 4 pages http://cancerres.aacijournals.org/content/77/13_Supplement/5387.

Pharo, et al., "Experimental factors affecting the robustness of DNA methylation Analysis," Scientific Reports, 6:33936, Sep. 27, 2016, 9 pages.

Pharo, et al., "A robust internal control for high-precision DNA methylation analyses by droplet digital PCR," Clinical Epigenetics (2018) 10:24, BioMed Central, 10 pages https://doi.org/10.1186/s13148-018-0456-5.

Sykes, et al., "Quantitation of Targets for PCR by se of Limiting Dilution," BioTechniques vol. 13, No. 3, 1992, pp. 444-449.

Trypsteen, et al., "ddpcRquant: threshold determination for single channel droplet digital PCR experiments," Anal Bioanal Chem (2015) 407, May 29, 2015, pp. 5827-5834.

Uehiro, et al., "Circulating cell-free DNA-based epigenetic assay can detect early breast cancer," Breast Cancer Research 18:129, Dec. 19, 2016, 14 pages.

Weisenberger, et al., "DNA methylation analysis by digital bisulfite genomic sequencing and digital MethyLight," Nucleic Acids Research, vol. 36, No. 14, Jul. 15, 2008, pp. 4689-4698.

Yu, et al., "MethyLight droplet digital PCR for detection and absolute quantification of infrequently methylated alleles," Epigenetics, 10:9, 803-809, Aug. 1, 2015, 8 pages.

Zhao, et al., "Cloning and Characterization of Human Synaptotagmin 10 Gene*," DNA Sequence, 14:5, 393-398, Jul. 11, 2009, 7 pages.

International Search Report and Written Opinion of corresponding PCT/EP2019/083147, dated Feb. 13, 2019, 16 pages.

Combined Search and Examination Report of corresponding GB 1720088.2, dated Aug. 29, 2018, 7 pages.

A)

B)

A)

B)

A)

B)

SEQUENCE LISTING

<160> NUMBER OF SEQ ID NOS: 80

<210> SEQ ID NO 1
<211> LENGTH: 31
<212> TYPE: DNA

<213> ORGANISM: Homo sapiens

<400> SEQUENCE: 1
gaggtaaatg taggtttta gtgttgattt t                31

<210> SEQ ID NO 2
<211> LENGTH: 33
<212> TYPE: DNA
<213> ORGANISM: Homo sapiens

<400> SEQUENCE: 2
ctttatcctc ccaatactaa ttattatttc tcc             33

<210> SEQ ID NO 3
<211> LENGTH: 20
<212> TYPE: DNA
<213> ORGANISM: Homo sapiens

<400> SEQUENCE: 3
agtatgggta tagaatttgt                            20

<210> SEQ ID NO 4
<211> LENGTH: 30
<212> TYPE: DNA
<213> ORGANISM: Homo sapiens

<400> SEQUENCE: 4
ggatttatta ggtgtgtaat gttatggatt                 30

<210> SEQ ID NO 5
<211> LENGTH: 31
<212> TYPE: DNA
<213> ORGANISM: Homo sapiens

<400> SEQUENCE: 5
actccacata aatcttctaa actaaattcc t                31

<210> SEQ ID NO 6
<211> LENGTH: 23
<212> TYPE: DNA
<213> ORGANISM: Homo sapiens

<400> SEQUENCE: 6
ttggttgaga ataaattggg ttt                        23

<210> SEQ ID NO 7
<211> LENGTH: 28
<212> TYPE: DNA
<213> ORGANISM: Homo sapiens

<400> SEQUENCE: 7
gtagttttag atggttttt gagttgga                    28

<210> SEQ ID NO 8
<211> LENGTH: 26
<212> TYPE: DNA
<213> ORGANISM: Homo sapiens

<400> SEQUENCE: 8
cactcccatc ctatcttccc tctata                     26

<210> SEQ ID NO 9
<211> LENGTH: 19

```
<212> TYPE: DNA
<213> ORGANISM: Homo sapiens

<400> SEQUENCE: 9
agggattaga gtaggtttg                                              19

<210> SEQ ID NO 10
<211> LENGTH: 22
<212> TYPE: DNA
<213> ORGANISM: Homo sapiens

<400> SEQUENCE: 10
tttgtatgtg gtgggagggt tt                                          22

<210> SEQ ID NO 11
<211> LENGTH: 23
<212> TYPE: DNA
<213> ORGANISM: Homo sapiens

<400> SEQUENCE: 11
acaaaaaaac acaccactcc caa                                         23

<210> SEQ ID NO 12
<211> LENGTH: 20
<212> TYPE: DNA
<213> ORGANISM: Homo sapiens

<400> SEQUENCE: 12
tatgtggaag tgtaataatg                                             20

<210> SEQ ID NO 13
<211> LENGTH: 94
<212> TYPE: DNA
<213> ORGANISM: Homo sapiens

<400> SEQUENCE: 13
gaggcaaatg caggttttcca gtgttgattt tagcatgggc acagaacctg ttttacaacg    60
aggagaaaca acaaccagca ttgggaggat aaag                                 94

<210> SEQ ID NO 14
<211> LENGTH: 99
<212> TYPE: DNA
<213> ORGANISM: Homo sapiens

<400> SEQUENCE: 14
ggacttacca ggtgtgcaat gtcatggacc acagtcaaaa caattggctg agaacaaact     60
gggtccccag gaactcagct cagaagattt atgtggagc                            99

<210> SEQ ID NO 15
<211> LENGTH: 100
<212> TYPE: DNA
<213> ORGANISM: Homo sapiens

<400> SEQUENCE: 15
gcagctccag atggcctcct gagctggacg accccaggtc tccagacatc tagggaccag     60
agcaggtttg gaacacagag ggaagacag gatgggagtg                           100

<210> SEQ ID NO 16
<211> LENGTH: 86
<212> TYPE: DNA
<213> ORGANISM: Homo sapiens
```

```
<400> SEQUENCE: 16
cttgtatgtg gtgggagggt ccatcccacg gcgcatgtgg aagtgcaaca atgccaccgt    60
tgactgggag tggtgtgctc ctttgc                                         86

<210> SEQ ID NO 17
<211> LENGTH: 568
<212> TYPE: DNA
<213> ORGANISM: Homo sapiens

<400> SEQUENCE: 17
ccacagttcc ttccgaagac acctgccgag gcaaatgcag gtttccagtg ttgattttag    60
catgggcaca gaacctgttt tacaacgagg agaaacaaca accagcattg ggaggataaa   120
gccagaactc tacaaacaga atcagttga ctctgagggc aaccaaaacg aagatgtcaa    180
aatctgtggg aaacttaact ttaccctcca gtatgattat gaaaatgaac ttctagttgt   240
taaaattatc aaagctttag atctccctgc taaagacttc acaggaactt ctgacccta    300 tgtgaagatg tatcttcttc cagataggaa aaagaaattt cagacccgcg tgcacagaaa   360
gactttaaat cctctatttg atgaaacttt tcaatttcct gtagcatatg atcaactaag   420
caaccgaaaa ctacatttca gtgtgtatga ttttgacaga ttttctagac atgacatgat   480
tggggaagtg attcttgata atttgtttga agtctctgat ctctccaggg aagccacagt   540
atggaaagat attcactgtg ctaccaca                                     568

<210> SEQ ID NO 18
<211> LENGTH: 661
<212> TYPE: DNA
<213> ORGANISM: Homo sapiens

<400> SEQUENCE: 18
tgggaagaga tcagtggtgt ggatgaacat tacacaccca tcaggactta ccaggtgtgc    60
aatgtcatgg accacagtca aaacaattgg ctgagaacaa actgggtccc caggaactca   120
gctcagaaga tttatgtgga gctcaagttc actctacgag actgcaatag cattccattg   180
gttttaggaa cttgcaagga gacattcaac ctgtactaca tggagtctga tgatgatcat   240
ggggtgaaat tcgagagca tcagtttaca aagattgaca ccattgcagc tgatgaaagt   300
ttcactcaaa tggatcttgg ggaccgtatt ctgaagctca cactgagat tagagaagta   360 ggtcctgtca caagaaggg atttttatttg gcatttcaag atgttggtgc ttgtgttgcc   420
ttggtgtctg tgagagtata cttcaaaaag tgcccattta cagtgaagaa tctggctatg   480
tttccagaca cggtacccat ggactcccag tccctggtgg aggttagagg gtcttgtgtc   540
aacaattcta aggaggaaga tcctccaagg atgtactgca gtacagaagg cgaatggctt   600
gtacccattg gcaagtgttc ctgcaatgct ggctatgaag aaagaggttt tatgtgccaa   660
g                                                                   661

<210> SEQ ID NO 19
<211> LENGTH: 1654
<212> TYPE: DNA
<213> ORGANISM: Homo sapiens

<400> SEQUENCE: 19
ccgccagctg agacgatgg tggaccactt ggccaacacg gagatcaaca gccagcgcat    60
cgcggcagtg gagagctgct tcggggcctc ggggcagccg ctggcgctgc caggccgagt   120
gctgctgggc gagggcgtgc tgaccaaaga gtgccgcaag aaggccaagc cgcgcatctt   180
```

-continued

```
cttcctctttt aacgacatcc tggtgtatgg cagcatcgtg ctcaacaagc gcaagtaccg    240
cagccagcac atcatccccc tggaggaggt cacactggag ctgttgccgg agacgctgca    300
ggccaagaac cgctggatga tcaagacggc caagaagtcc tttgtggtgt cggccgcctc    360
cgctacggag cgccaggaat ggattagcca catcgaggag tgcgtgcggc ggcaactgag    420
ggccacgggc cgcccgccca gcacggagca cgcggcaccc tggatccccg acaaggccac    480
ggacatctgc atgcgctgca cgcagacgcg cttctctgcc ctcacgaggc gccaccactg    540
ccgcaagtgc ggcttcgtgg tctgcgctga gtgctcgcgc cagcgcttcc tgctcccgcg    600
cctgtccccc aagcccgtgc gcgtctgcag cctctgctac cgcgaactgg ccgcccagca    660
gcggcaggag gaggcggagg agcagggcgc ggggtcccca gggcagccag cccacctggc    720
ccggcccatc tgcggagcgt ccagtggaga tgacgatgac tccgacgagg acaaggaggg    780
cagcagggac ggcgactggc ccagcagcgt ggagttctac gcctcggggg tggcctggtc    840
tgccttccac agctgacccc cggcctgcag aacatctgtc cccaagccag ctccactgcc    900
caggccccca gagggcagc tccagaagct gcccagggct ccgggacccc atcccatggt    960
ggcaggtgca gcggtgggga gtggctcttt ctggactccc agtgcctttt tgctggacac   1020
tgtgtcctta tggcttcact gcaggtaatg cctttcccct caggaagccc cagaacaccc   1080
acaggtcttg gtaacaaacg ccaccttaca ctctgcaggc tgcagcggca gctccagatg   1140
gcctcctgag ctggacgacc ccaggtctcc agacatctag ggaccagagc aggtttggga   1200
acacagaggg aagacaggat gggagtgtag ccacagaacc cacctgcacc ctgacaggca   1260 cacccactg aagagcctga gtcccaggag gcctcctgga agcccaggac tgcccaccca   1320
ccacgctggt gcccaccgcc tggccagcca agccctgccg atcagacatg tgggctcccc   1380
gaagcccagc cagagactgc cgtgctgtgg gtgccaccag gccagggac tgcagcctga   1440 gctccccgag gccagggca gccggtgag gactctgtcc tgtgtcacct ctctccaggt   1500
gtccagctgt ctcatgcctt tttgtcctgt cctcagctct ccgtgtggtc agcgaaacca   1560
ttgttttctg ttaggactca gttgcaagaa cagaaaccct gcccccactt aataataaaa   1620
aagaaagttt attgatgggt ggttgcaaaa caaa                              1654
```

<210> SEQ ID NO 20
<211> LENGTH: 86
<212> TYPE: DNA
<213> ORGANISM: Artificial Sequence
<220> FEATURE:
<223> OTHER INFORMATION: Product of bisulphite treatment of SEQ ID NO:
      16

<400> SEQUENCE: 20

```
uttgtatgtg gtgggagggt uuatuuuacg gcguatgtgg aagtguaaua atguuaucgt    60
tgautgggag tggtgtgutu utttgu                                          86
```

<210> SEQ ID NO 21
<211> LENGTH: 1594
<212> TYPE: DNA
<213> ORGANISM: Homo sapiens

<400> SEQUENCE: 21

```
gaaattgggg agaatgtgca catttacctg attgggaaag agtcatctcg tacccactcg    60
ttggctgtgt ccttgcactg tgcagaagat gactccatca gtgtaagtgg ccaaaacagt   120
ttgtgccacc agatcactgc ggcctgcaag catggtggag acttgtatgt ggtgggaggg   180
```

```
tccatcccac ggcgcatgtg gaagtgcaac aatgccaccg ttgactggga gtggtgtgct        240
cctttgcctc gggaccggct ccagcacacc ctggtgtctg tgcccgggaa agatgccata        300
tattcactgg gtggcaagac actgcaagat accctctcca acgcagtcat ttattatcgc        360
gtaggtgata atgtgtggac agagacaact cagctagagg tggctgtgtc aggggctgct        420
ggtgccaacc tcaacgggat catctactta ctagggggga aggagaatga tctgacttc         480 tttaccaaac cttcccgact catccagtgc tttgacacag agacagacaa atgccatgtg        540
aagccctatg tgctgcccct tgcaggccgc atgcacgcag ctgtgcataa agatctggtg        600
ttcatcgtgg ctgaagggga ctccctggtg tgctacaatc ccttgctaga cagcttcacc        660 cggcttttgcc ttcctgaggc ctggagctct gccccatccc tctggaagat tgccagctgt       720
aacgggagca tctatgtctt ccgggaccga tataaaaagg gggatgccaa cacctacaag        780
cttgaccctg ccacttcagc cgtaactgtc acaagaggta ttaaggtgct gcttaccaat        840
ttgcagtttg tgttggccta aggctgtggg gaggggagga gaactgctca ctccttttcc        900
ctccccatac aaactcaaag tcccctgggc cccaattcag agttatgttt tttttggcac        960
atactagaaa ggcagtgcct cagcccttcc ctgaatccat ggaggtgttc tgtttggggc       1020
tttttagact gctgctgctc agctggttgc ttgaactgac agtaggccag cctgttctct       1080
gccattccct agtcatcctg tgcctcacca cagcttgctt agagcaagcc ttttctcaga       1140
ccttaggcac agcctctcct ctttacctga tcaatgttaa atgtaagcac ccctgatccc       1200
aggacataag gaaagatgcc caattgtact tttgttctat agcctgtgaa atggctagtt       1260
gatcattttt ccacaaagaa ttaggtgtta agagttttcc ttcaggcttt acttaggaga       1320
atggactaag ctgaaggtgt acttcaccag caagagtcaa ctctagaatt caggatgttc       1380
cttctattgt tttcttatcc atctgtcagg aaatgtaact ttggttttat ttttggctta       1440
ttccaagggg taagccagaa aatagaaatg attatttctg attaatagca gaaacttttt       1500
caatctcaaa tatataaggt gtctgctctt ttaaaagctc taagctaagt caagagctag       1560
gaactgttga tacaaataaa agttttttgaa ggga                                  1594
```

<210> SEQ ID NO 22
<211> LENGTH: 27
<212> TYPE: DNA
<213> ORGANISM: Homo sapiens

<400> SEQUENCE: 22

```
ggattatwtt tttgtttgga ggttaga                                             27
```

<210> SEQ ID NO 23
<211> LENGTH: 24
<212> TYPE: DNA
<213> ORGANISM: Homo sapiens

<400> SEQUENCE: 23

```
caaccttcaa attctccttc ttcc                                                24
```

<210> SEQ ID NO 24
<211> LENGTH: 20
<212> TYPE: DNA
<213> ORGANISM: Homo sapiens

<400> SEQUENCE: 24

```
gtttttgttt tgaaggtttg                                                     20
```

```
<210> SEQ ID NO 25
<211> LENGTH: 25
<212> TYPE: DNA
<213> ORGANISM: Homo sapiens

<400> SEQUENCE: 25
atgggtgatg ttgagaaagg taaga                                   25

<210> SEQ ID NO 26
<211> LENGTH: 36
<212> TYPE: DNA
<213> ORGANISM: Homo sapiens

<400> SEQUENCE: 26
actatataaa aatatccatt ttcctaacct atcttc                       36

<210> SEQ ID NO 27
<211> LENGTH: 28
<212> TYPE: DNA
<213> ORGANISM: Homo sapiens

<400> SEQUENCE: 27
agtataagat tgggttaaat ttttatgg                                28

<210> SEQ ID NO 28
<211> LENGTH: 27
<212> TYPE: DNA
<213> ORGANISM: Homo sapiens

<400> SEQUENCE: 28
gagattttgg ataatgggaa gtttttt                                 27

<210> SEQ ID NO 29
<211> LENGTH: 24
<212> TYPE: DNA
<213> ORGANISM: Homo sapiens

<400> SEQUENCE: 29
accataccac ttatcaaccc aacc                                    24

<210> SEQ ID NO 30
<211> LENGTH: 21
<212> TYPE: DNA
<213> ORGANISM: Homo sapiens

<400> SEQUENCE: 30
ttttggattt ggatgaggtt a                                       21

<210> SEQ ID NO 31
<211> LENGTH: 28
<212> TYPE: DNA
<213> ORGANISM: Homo sapiens

<400> SEQUENCE: 31
ggaatatttg atgaggttgt attttttgg                               28

<210> SEQ ID NO 32
<211> LENGTH: 24
<212> TYPE: DNA
<213> ORGANISM: Homo sapiens

<400> SEQUENCE: 32
ctttccacca aaaatacaac ctca                                    24
```

<210> SEQ ID NO 33
<211> LENGTH: 25
<212> TYPE: DNA
<213> ORGANISM: Homo sapiens

<400> SEQUENCE: 33
tttgatatag ttgaaagttt ggtgg                                          25

<210> SEQ ID NO 34
<211> LENGTH: 26
<212> TYPE: DNA
<213> ORGANISM: Homo sapiens

<400> SEQUENCE: 34
ggtatttgag agatgtgttt gaggtg                                         26

<210> SEQ ID NO 35
<211> LENGTH: 22
<212> TYPE: DNA
<213> ORGANISM: Homo sapiens

<400> SEQUENCE: 35
tccccatcaa accaaacaaa ac                                             22

<210> SEQ ID NO 36
<211> LENGTH: 22
<212> TYPE: DNA
<213> ORGANISM: Homo sapiens

<400> SEQUENCE: 36
ataatttaag gggaggagat ta                                             22

<210> SEQ ID NO 37
<211> LENGTH: 30
<212> TYPE: DNA
<213> ORGANISM: Homo sapiens

<400> SEQUENCE: 37
gaagtttttt gagggtattt aagtattgga                                     30

<210> SEQ ID NO 38
<211> LENGTH: 24
<212> TYPE: DNA
<213> ORGANISM: Homo sapiens

<400> SEQUENCE: 38
acctcataat caaaaaaacc ccct                                           24

<210> SEQ ID NO 39
<211> LENGTH: 20
<212> TYPE: DNA
<213> ORGANISM: Homo sapiens

<400> SEQUENCE: 39
agttgtttgg ggattatgtt                                                20

<210> SEQ ID NO 40
<211> LENGTH: 29
<212> TYPE: DNA
<213> ORGANISM: Homo sapiens

<400> SEQUENCE: 40
tttagggatt tattgttagg taggagttg                                          29

<210> SEQ ID NO 41
<211> LENGTH: 33
<212> TYPE: DNA
<213> ORGANISM: Homo sapiens

<400> SEQUENCE: 41
cttctcctac aactacttct aaatactacc aaa                                     33

<210> SEQ ID NO 42
<211> LENGTH: 22
<212> TYPE: DNA
<213> ORGANISM: Homo sapiens

<400> SEQUENCE: 42
tgtttaaggt ggataatttt gt                                                 22

<210> SEQ ID NO 43
<211> LENGTH: 27
<212> TYPE: DNA
<213> ORGANISM: Homo sapiens

<400> SEQUENCE: 43 tgggatagggg agtaggttat gttaggt                                           27

<210> SEQ ID NO 44
<211> LENGTH: 20
<212> TYPE: DNA
<213> ORGANISM: Homo sapiens

<400> SEQUENCE: 44 aaacccacc cacaccaaac                                                     20

<210> SEQ ID NO 45
<211> LENGTH: 22
<212> TYPE: DNA
<213> ORGANISM: Homo sapiens

<400> SEQUENCE: 45
tggtgaaagt ttttagtttg tg                                                 22

<210> SEQ ID NO 46
<211> LENGTH: 27
<212> TYPE: DNA
<213> ORGANISM: Homo sapiens

<400> SEQUENCE: 46 gttttagtt ttttgtgtga agggttt                                             27

<210> SEQ ID NO 47
<211> LENGTH: 25
<212> TYPE: DNA
<213> ORGANISM: Homo sapiens

<400> SEQUENCE: 47
aaaactcaac aacaaaatcc aaacc                                              25

<210> SEQ ID NO 48
<211> LENGTH: 25
<212> TYPE: DNA
<213> ORGANISM: Homo sapiens

<400> SEQUENCE: 48

-continued ttattaagga gttgtttgta gggaa   25

<210> SEQ ID NO 49
<211> LENGTH: 28
<212> TYPE: DNA
<213> ORGANISM: Homo sapiens

<400> SEQUENCE: 49
gatgaggaag atggagagaa tgtttatt   28

<210> SEQ ID NO 50
<211> LENGTH: 34
<212> TYPE: DNA
<213> ORGANISM: Homo sapiens

<400> SEQUENCE: 50
ctctatccac tataaaaact atccataaaa tcac   34

<210> SEQ ID NO 51
<211> LENGTH: 19
<212> TYPE: DNA
<213> ORGANISM: Homo sapiens

<400> SEQUENCE: 51
agtgattttg tgattggga   19

<210> SEQ ID NO 52
<211> LENGTH: 29
<212> TYPE: DNA
<213> ORGANISM: Homo sapiens

<400> SEQUENCE: 52
gagatatata gtgttgagga tgttgggag   29

<210> SEQ ID NO 53
<211> LENGTH: 32
<212> TYPE: DNA
<213> ORGANISM: Homo sapiens

<400> SEQUENCE: 53
cttcttccat ctactataaa attttctcca tc   32

<210> SEQ ID NO 54
<211> LENGTH: 23
<212> TYPE: DNA
<213> ORGANISM: Homo sapiens

<400> SEQUENCE: 54
aagtaatagg atgtgtagaa gga   23

<210> SEQ ID NO 55
<211> LENGTH: 25
<212> TYPE: DNA
<213> ORGANISM: Homo sapiens

<400> SEQUENCE: 55
tggtgatgga ggaggtttag taagt   25

<210> SEQ ID NO 56
<211> LENGTH: 27
<212> TYPE: DNA
<213> ORGANISM: Homo sapiens

<400> SEQUENCE: 56
aaccaataaa acctactcct cccttaa    27

<210> SEQ ID NO 57
<211> LENGTH: 30
<212> TYPE: DNA
<213> ORGANISM: Homo sapiens

<400> SEQUENCE: 57
accaccaccc aacacacaat aacaaacaca    30

<210> SEQ ID NO 58
<211> LENGTH: 26
<212> TYPE: DNA
<213> ORGANISM: Homo sapiens

<400> SEQUENCE: 58
ttgtatgtat gtgagtgtgg gagaga    26

<210> SEQ ID NO 59
<211> LENGTH: 22
<212> TYPE: DNA
<213> ORGANISM: Homo sapiens

<400> SEQUENCE: 59
tttcttccac cccttctctt cc    22

<210> SEQ ID NO 60
<211> LENGTH: 18
<212> TYPE: DNA
<213> ORGANISM: Homo sapiens

<400> SEQUENCE: 60
ctccccctct aactctat    18

<210> SEQ ID NO 61
<211> LENGTH: 20
<212> TYPE: DNA
<213> ORGANISM: Homo sapiens

<400> SEQUENCE: 61
cgaattatag cggcggaggt    20

<210> SEQ ID NO 62
<211> LENGTH: 19
<212> TYPE: DNA
<213> ORGANISM: Homo sapiens

<400> SEQUENCE: 62
aaatcgcgta aactccgcg    19

<210> SEQ ID NO 63
<211> LENGTH: 16
<212> TYPE: DNA
<213> ORGANISM: Homo sapiens

<400> SEQUENCE: 63
cgttaggtcg ggcggt    16

<210> SEQ ID NO 64
<211> LENGTH: 21
<212> TYPE: DNA
<213> ORGANISM: Homo sapiens -continued

```
<400> SEQUENCE: 64
cgcgcgattc gttgtttatt a                                              21

<210> SEQ ID NO 65
<211> LENGTH: 19
<212> TYPE: DNA
<213> ORGANISM: Homo sapiens

<400> SEQUENCE: 65
ccaacccaac acccacctt                                                 19

<210> SEQ ID NO 66
<211> LENGTH: 16
<212> TYPE: DNA
<213> ORGANISM: Homo sapiens

<400> SEQUENCE: 66
ggatttcgcg gttaac                                                    16

<210> SEQ ID NO 67
<211> LENGTH: 25
<212> TYPE: DNA
<213> ORGANISM: Homo sapiens

<400> SEQUENCE: 67
ggtcgagttt tagtcggagt tacgt                                          25

<210> SEQ ID NO 68
<211> LENGTH: 24
<212> TYPE: DNA
<213> ORGANISM: Homo sapiens

<400> SEQUENCE: 68
cccgaaaacg aaacgtaaaa acta                                           24

<210> SEQ ID NO 69
<211> LENGTH: 23
<212> TYPE: DNA
<213> ORGANISM: Homo sapiens

<400> SEQUENCE: 69
cgtatttata gtttgggtag cgc                                            23

<210> SEQ ID NO 70
<211> LENGTH: 94
<212> TYPE: DNA
<213> ORGANISM: Artificial Sequence
<220> FEATURE:
<223> OTHER INFORMATION: Product of amplification of SEQ ID NO: 74

<400> SEQUENCE: 70
gaggtaaatg taggttttta gtgttgattt tagtatgggt atagaatttg ttttataacg    60
aggagaaata ataattagta ttgggaggat aaag                                94

<210> SEQ ID NO 71
<211> LENGTH: 99
<212> TYPE: DNA
<213> ORGANISM: Artificial Sequence
<220> FEATURE:
<223> OTHER INFORMATION: Product of amplification of SEQ ID NO: 75

<400> SEQUENCE: 71
```

```
ggatttatta ggtgtgtaat gttatggatt atagttaaaa taattggttg agaataaatt    60
gggtttttag gaatttagtt tagaagattt atgtggagt                           99

<210> SEQ ID NO 72
<211> LENGTH: 100
<212> TYPE: DNA
<213> ORGANISM: Artificial Sequence
<220> FEATURE:
<223> OTHER INFORMATION: Product of amplification of SEQ ID NO: 76

<400> SEQUENCE: 72
gtagttttag atggtttttt gagttggacg attttaggtt tttagatatt tagggattag    60
agtaggtttg ggaatataga gggaagatag gatgggagtg                         100

<210> SEQ ID NO 73
<211> LENGTH: 86
<212> TYPE: DNA
<213> ORGANISM: Artificial Sequence
<220> FEATURE:
<223> OTHER INFORMATION: Product of amplification of SEQ ID NO: 20

<400> SEQUENCE: 73
tttgtatgtg gtgggagggt ttattttacg gcgtatgtgg aagtgtaata atgttatcgt    60
tgattgggag tggtgtgttt ttttgt                                         86

<210> SEQ ID NO 74
<211> LENGTH: 94
<212> TYPE: DNA
<213> ORGANISM: Artificial Sequence
<220> FEATURE:
<223> OTHER INFORMATION: Product of bisulphite-treatment of SEQ ID NO:
      13

<400> SEQUENCE: 74
gagguaaatg uaggttttuua gtgttgattt taguatgggu auagaauutg ttttauaacg    60
aggagaaaua auaauuagua ttgggaggat aaag                                94

<210> SEQ ID NO 75
<211> LENGTH: 99
<212> TYPE: DNA
<213> ORGANISM: Artificial Sequence
<220> FEATURE:
<223> OTHER INFORMATION: Product of bisulphite treatment of SEQ ID NO:
      14

<400> SEQUENCE: 75
ggauttauua ggtgtguaat gtuatggauu auagtuaaaa uaattggutg agaauaaaut    60
gggtuuuuag gaautuagut uagaagattt atgtggagu                           99

<210> SEQ ID NO 76
<211> LENGTH: 100
<212> TYPE: DNA
<213> ORGANISM: Artificial Sequence
<220> FEATURE:
<223> OTHER INFORMATION: Product of bisulphite treatment of SEQ ID NO:15

<400> SEQUENCE: 76
guagutuuag atgguutuut gagutggacg auuuuaggtu tuuagauatu tagggauuag    60
aguaggtttg ggaauauaga gggaagauag gatgggagtg                         100

<210> SEQ ID NO 77
<211> LENGTH: 1594
```

<212> TYPE: DNA
<213> ORGANISM: Homo sapiens

<400> SEQUENCE: 77

```
aagaccagcc tgggcaacat agcaagactc tgtctctaca aaaaatttaa aaattaactg      60
ggcaggtgtg gtggcacatg cctgtagtcc cagctactca ggaggcggag gccagaggat     120
ggcttgagct caggagtttt aagctacagt gagctataat agcactaccg tactccagct     180
agggtgacag aacaagatcc tgtctcaaaa acaaaaaac aaaacaaaac aaacaaacaa      240
aaagaacatt taagtgtttc agatgttctg gaattttagg agacttctct ttgaatattg     300
tacttcttta tttttcaaa agtacctctt tgattatatg tatgtgtcta tctatgtaga      360
tatagatatc ttttcactat tctgggggtg gggaagagtt tatatgtcac tgtataacat    420
tctcatcaaa atgatctccc tcaatgattt tgtgtatatg tgtgtgtgtt cagccacagt     480
tccttccgaa gacacctgcc gaggcaaatg caggtttcca gtgttgattt tagcatgggc    540
acagaacctg tttacaacg aggagaaaca acaaccagca ttgggaggat aaagccagaa      600
ctctacaaac agaaatcagt tgactctgag ggcaaccaaa acgaagatgt caaaatctgt    660
gggaaactta actttacccct ccagtatgat tatgaaaatg aacttctagt tgttaaaatt    720
atcaaagctt tagatctccc tgctaaagac ttcacaggaa cttctgaccc ttatgtgaag    780
atgtatcttc ttccagatag gaaaaagaaa tttcagaccc gcgtgcacag aaagacttta    840
aatcctctat ttgatgaaac ttttcaattt cctgtagcat atgatcaact aagcaaccga    900
aaactacatt tcagtgtgta tgattttgac agatttccta gacatgacat gattggggaa    960
gtgattcttg ataatttgtt tgaagtctct gatctctcca gggaagccac agtatggaaa   1020
gatattcact gtgctaccac agtaagtagt aattccacca atatattgtt ttttatttga   1080
cttacaatgc tatgtgacta attattaccc aaattatcgg aataagcctt gcagagttat   1140
ggaatttatg tctaagatcc tgcaaaggta gaatttcatt tctactaata ataattcagg   1200
cacctaatgc tgaatatact agtaaccccta gtgattgtgt gaataaaaaa acgtagctct   1260
tataaattag cagaactggt aggctatttc tcctttaaaa tattcatctg taatataaat   1320
atcctatctg cagcaccaag tttcctcaca gttagtattg actttcatta tttaaggtaa   1380
ttttgttatt ttcattattt tagaaattat ttcactcttt aagaataatg acttcattat   1440
ttaagataat tcatcagatc aaacctaaaa tgtactttga tgctatttgg aaaagtcctt   1500
ggtttgatct gaaacaaccc attatttcag aagctttcag ggaatacaca caattacaat   1560
atatgaaatg atcagtgatc aagaagtaat catt                               1594
```

<210> SEQ ID NO 78
<211> LENGTH: 1599
<212> TYPE: DNA
<213> ORGANISM: Homo sapiens

<400> SEQUENCE: 78

```
atattcactt tattttacct tatatcaatt ttaccaaaaa cctggcacaa attgggaaaa      60
gattaataag catgaatttt aggcagtatt attaattttt tcttttttaa actgagaaaa     120
acacccaaaa acatatgaga aaataatatt atagtgtcat ggagacaac tgatttgagg       180
ttttgatcct ggaatgtttg attaggctct attaactgct aagtgtcttt tcctgaata      240
ttcaacaaac tgtaacgcaa ttgaaatgtg ttcatcaaaa ttataaatta ctttatgtcc     300
attaactcag agaaccttgc aaataaaaac tacaaacaag aatgttttta atgagtaaat    360
```

```
gatgatttat tatatagaga tggctctgac acccttatgt tgtattcgtt attatcatta        420
attctgcctc actctctgtt tctctttgat tcttcagtgg gaagagatca gtggtgtgga        480
tgaacattac acaccatca ggacttacca ggtgtgcaat gtcatggacc acagtcaaaa         540
caattggctg agaacaaact gggtccccag gaactcagct cagaagattt atgtggagct        600
caagttcact ctacgagact gcaatagcat tccattggtt ttaggaactt gcaaggagac        660
attcaacctg tactcatgg agtctgatga tgatcatggg gtgaaatttc gagagcatca        720
gtttacaaag attgacacca ttgcagctga tgaaagtttc actcaaatgg atcttgggga       780
ccgtattctg aagctcaaca ctgagattag agaagtaggc cctgtcaaca agaagggatt       840
ttatttggca tttcaagatg ttggtgcttg tgttgccttg gtgtctgtga gagtatactt        900
caaaaagtgc ccatttacag tgaagaatct ggctatgttt ccagacacgg tacccatgga       960
ctcccagtcc ctggtggagg ttagagggtc ttgtgtcaac aattctaagg aggaagatcc       1020
tccaaggatg tactgcagta cagaaggcga atggcttgta cccattggca agtgttcctg      1080
caatgctggc tatgaagaaa gaggttttat gtgccaaggt aagagccttc tctattttc        1140 tttgagcaat atttctcacc tatgagttta tcatagtgtc attaaatgaa atgcactcag       1200
tctcaactca cttggcagga aaacatgcct caaactgacc atagtctatt tatggactaa      1260
aattaattcc atttgatgtg gtaattcatg ctttgctgta gaaatattaa tgtatttgat        1320
tatacagtgc tggcctgcac cctgtaatag gtgttataca tgctatattt aagttttct        1380 gctgtttaat aactaaggta atctaattct agaccacctg gaagaaaaac attctatctc       1440
ttttatgtag aaagttgaga aatctttagc actcagctaa cctaattcta acagaattag      1500
atactgtggt ggttatttat gctggtgctc atctatctca tagcaatatt tacttcattg       1560
ctataaagta cagtcttttc ttcactgaca tctgggtat                               1599

<210> SEQ ID NO 79
<211> LENGTH: 2711
<212> TYPE: DNA
<213> ORGANISM: Homo sapiens

<400> SEQUENCE: 79
gggctgaacc tctgccctct gctgcccaca gtagtagccg gctcagtagc actttttttt        60
tttaagagat agaatccact cagtcaccta gctagagtgt agtggcatga tcatagctca       120
ctgtagcctc aaactcctgg gctcgagcct cctcttgcct cagccttcca aaacgctgga      180
accacaggca tgaaccgctg cacctggcct aagtagcaca ctttatcact gccttcccat       240
ccctgtctgg cctccacatc cctttactg ggaaatcccc cttccctccc cgtagttccc        300
tgtactcccg tctaagggtc agcttccgag gtgatgcttc tcagtgctgg gcaggcctgc      360
gggttactgt gcgtagtcag tgggctgcct ggcatggtgg gttagtcagt tgggggtggg      420
cagcgtggtt ctgacacccc catgcctgag cctggacata ctccttgtct gtctcctcct       480
gcagccgcca gctggagacg atggtggacc acttggccaa cacggagatc aacagccagc      540
gcatcgcggc agtggagagc tgcttcgggg cctcggggca gccgctggcg ctgccaggcc       600
gagtgctgct gggcgagggc gtgctgacca aagagtgccg caagaaggcc aagccgcgca      660
tcttcttcct cttttaacgac atcctggtgt atggcagcat cgtgctcaac aagcgcaagt        720
accgcagcca gcacatcatc cccctggagg aggtcacact ggagctgttg ccggagacgc       780
tgcaggccaa gaaccgctgg atgatcaaga cggccaagaa gtccttttgtg gtgtcggccg     840 cctccgctac ggagcgccag gaatggatta gccacatcga ggagtgcgtg cggcggcaac       900
```

```
tgagggccac gggccgcccg cccagcacgg agcacgcggc accctggatc cccgacaagg    960
ccacggacat ctgcatgcgc tgcacgcaga cgcgcttctc tgccctcacg aggcgccacc   1020
actgccgcaa gtgcggcttc gtggtctgcg ctgagtgctc cgccagcgc ttcctgctcc    1080 cgcgcctgtc ccccaagccc gtgcgcgtct gcagcctctg ctaccgcgaa ctggccgccc   1140
agcagcggca ggaggaggcg gaggagcagg gcgcggggtc cccagggcag ccagcccacc   1200
tggcccggcc catctgcgga gcgtccagtg agatgacga tgactccgac gaggacaagg    1260
agggcagcag ggacggcgac tgcccagca gcgtggagtt ctacgcctcg ggggtggcct    1320
ggtctgcctt ccacagctga ccccggcct gcagaacatc tgtccccaag ccagctccac    1380
tgcccaggcc cccaagaggg cagctccaga agctgcccag gctccggga ccccatccca    1440 tggtggcagg tgcagcggtg gggagtggct ctttctggac tcccagtgcc ttttgctgg    1500 acactgtgtc cttatggctt cactgcaggt aatgcctttc ccttcaggaa gccccagaac   1560
acccacaggt cttggtaaca aacgccacct tacactctgc aggctgcagc ggcagctcca   1620
gatggcctcc tgagctggac daccccaggt ctccagacat ctagggacca gagcaggttt    1680
gggaacacag agggaagaca ggatgggagt gtagccacag aacccacctg caccctgaca    1740
ggcacacccc actgaagagc ctgagtccca ggaggcctcc tggaagccca ggactgccca    1800
cccaccacgc tggtgcccac cgcctggcca gccaagccct gccgatcaga catgtgggct    1860
ccccgaagcc cagccagaga ctgccgtgct gtgggtgcca ccaggcccag ggactgcagc    1920
ctgagctccc cgaggcccag ggcagccggg tgaggactct gtcctgtgtc acctctctcc    1980
aggtgtccag ctgtctcatg cctttttgtc ctgtcctcag ctctccgtgt ggtcagcgaa    2040
accattgttt tctgttagga ctcagttgca agaacagaaa ccctgccccc acttaataat    2100
aaaaaagaaa gtttattgat gggtggttgc aaaacaaacc caggagtgtc cttgcttcag    2160
acatggctct gtccatggtt gaaaatgtgc taggtggcaa aaatctacca ctgtcccca    2220 cactgggagt tcttgtgtat gctggctgcc tgaaggagac agacgctcat gctgtgcctt    2280
ggctgggctc ccccaggaca caggtctgtc cgggtgccat gaccgtgcc tgatgcctgc    2340 tgccctattc actttggtgt gggcgatctc agtggatgga actgaggaaa caaatagcca    2400
tttgtgtggc tctgccgggc ctcccaggct gagagcttcc ccgtgcagtc ctgcctggcc    2460
ctggggctgg tgctatggag agggaaactg gccccaggt acaccagcct ttctcagagt    2520
gagtgtgcat tgggcctggg gctcgaggtc agcctcccaa cgcctggccc catgctggcc    2580
atggaactgg ggatccttta acagtgtccc acgagtgctt ctgcactagt ctttcccagc    2640
gcctcagcct tggcaggact ggggcatgga ctggggttgc tgtcagctag aagtggtgac    2700
cgtggggctg g                                                         2711
```

<210> SEQ ID NO 80
<211> LENGTH: 1933
<212> TYPE: DNA
<213> ORGANISM: Homo sapiens

<400> SEQUENCE: 80

```
aaggatgtct ttgtaacccc agtaccacca atctatgagc tttcaaagtt ccttgagaac      60
tactgtcatc aagttaacaa tcttaatcac ccttttgtctg aagcactagc ttatgagagt    120
tttttaaaag ctacaaggat gaatacaaca gattctccgc ccggcataaa ttgcctcaaa    180
gaaagtgact agaggagagt tggatgccat acagtaatta gagagtagta tgataaagct    240
```

-continued

```
aggaacaagt gtgagggcca ggatcttaag gatatgtgtc ttagctgagc cttagcctag    300
aatttaacag ctgtcatata attttaattt tgccaatagg aaattgggga gaatgtgcac    360
atttacctga ttgggaaaga gtcatctcgt acccactcgt tggctgtgtc cttgcactgt    420
gcagaagatg actccatcag tgtaagtggc caaaacagtt tgtgccacca gatcactgcg    480
gcctgcaagc atggtggaga cttgtatgtg gtgggagggt ccatcccacg gcgcatgtgg    540
aagtgcaaca atgccaccgt tgactgggag tggtgtgctc cttgcctcg ggaccggctc    600 cagcacaccc tggtgtctgt gcccgggaaa gatgccatat attcactggg tggcaagaca    660
ctgcaagata ccctctccaa cgcagtcatt tattatcgcg taggtgataa tgtgtggaca    720
gagacaactc agctagaggt ggctgtgtca ggggctgctg gtgccaacct caacgggatc    780
atctacttac tagggggga ggagaatgat ctggacttct ttaccaaacc ttcccgactc    840
atccagtgct ttgacacaga gacagacaaa tgccatgtga agccctatgt gctgcccttt    900
gcaggccgca tgcacgcagc tgtgcataaa gatctggtgt tcatcgtggc tgaaggggac    960
tccctggtgt gctacaatcc cttgctagac agcttcaccc ggctttgcct tcctgaggcc   1020
tggagctctg ccccatccct ctggaagatt gccagctgta acgggagcat ctatgtcttc   1080
cgggaccgat ataaaaaggg ggatgccaac acctacaagc ttgaccctgc cacttcagcc   1140
gtaactgtca caagaggtat taaggtgctg cttaccaatt tgcagtttgt gttggcctaa   1200
ggctgtgggg aggggaggag aactgctcac tccttttccc tccccataca aactcaaagt   1260
cccctgggcc ccaattcaga gttatgtttt ttttggcaca tactagaaag gcagtgcctc   1320
agcccttccc tgaatccatg gaggtgttct gtttggggct ttttagactg ctgctgctca   1380
gctggttgct tgaactgaca gtaggccagc ctgttctctg ccattcccta gtcatcctgt   1440
gcctcaccac agcttgctta gagcaagcct tttctcagac cttaggcaca gcctctcctc   1500
tttacctgat caatgttaaa tgtaagcacc cctgatccca ggacataagg aaagatgccc   1560
aattgtactt ttgttctata gcctgtgaaa tggctagttg atcatttttc cacaaagaat   1620
taggtgttaa gagttttcct tcaggcttta cttaggagaa tggactaagc tgaaggtgta   1680
cttcaccagc aagagtcaac tctagaattc aggatgttcc ttctattgtt ttcttatcca   1740
tctgtcagga aatgtaactt tggttttatt tttggcttat tccaaggggt aagccagaaa   1800
atagaaatga ttatttctga ttaatagcag aaactttttc aatctcaaat atataaggtg   1860
tctgctcttt taaaagctct aagctaagtc aagagctagg aactgttgat acaaataaaa   1920
gtttttgaag gga                                                      1933
```

PCR CONTROLS

CROSS-REFERENCE TO RELATED APPLICATION(S)

This application is a National Phase Patent Application and claims priority to and the benefit of International Application Number PCT/EP2018/083147, filed on Nov. 30, 2018, which claims priority to and the benefit of British Patent Application Number 1720088.2, filed Dec. 1, 2017, the entire contents of all of which are incorporated herein by reference.

SEQUENCE LISTING

The instant application contains a Sequence Listing submitted in ASCII format via EFS-Web and is incorporated herein by reference in its entirety. Said ASCII copy, which was last modified on May 29, 2020, is named "190735_SequenceListing_ST25.txt", and is 29,309 bytes in size.

The present invention is in the field of absolute nucleic acid quantification. The invention provides a method of quantification of a target nucleic acid using a particular set of control genes for normalisation. Also provided is a kit comprising one or more primer sets for use in such a method, and the use of an internal control in a method of amplification for absolute quantification of a target nucleic acid, using a particular set of control genes.

In modern molecular science the absolute quantification of nucleic acids in a sample is often necessary or desired. Absolute quantification of DNA is important in next generation sequencing (NGS), in which the concentrations of DNA library preparations prepared for sequencing must be quantified in order to include the appropriate amount of a DNA library in a sequencing reaction, thus maximising sequencing yield. Absolute quantification of nucleic acids also enables the detection of a nucleic acid which forms only a small proportion of a sample. For instance, absolute DNA quantification can be used to detect nucleic acid sequences or mutations which are indicative of cancer within a clinical sample comprising mainly healthy tissue, or to quantify the amount of a rare allele in a sample, or to determine the number of copies of e.g. viral DNA or RNA in a given sample. Absolute quantification of DNA can also be used in conjunction with methylation-specific PCR to quantify the proportion of a given methylation pattern for a particular nucleic acid sequence within a sample.

There are at present a relatively limited number of methods of absolute quantification of a nucleic acid. These are generally based on the polymerase chain reaction (PCR), which enables amplification of DNA. RNA may be analysed by PCR if first reverse transcribed into DNA.

One method by which absolute DNA quantification may be performed is absolute quantification quantitative PCR (qPCR). Using nucleic acid standards of known concentrations, a standard curve may be generated and used to quantify the amount of nucleic in a sample of interest.

Another method of absolute DNA concentration quantification is digital FOR (dPCR), in which a FOR mixture is randomly divided into a large number of partitions. Individual PCRs are performed inside each partition, and based on the number of fluorescence-positive partitions, the absolute quantity of the target can be calculated (Huggett et al., *Biomol Detect Quantif* 2015, 3:A1-5). The method thus avoids the requirement for a standard curve. The principle behind the method was described in 1992 (Sykes et al., *Biotechniques* 13(3): 444-449), but its use was for many years hampered by a lack of suitable protocols and instruments. Technological development during the last decade has led to several commercial systems for dPCR, and with the concomitant increase in liquid biopsy analyses for cancer screening, for detection of minimal residual disease after surgery and for monitoring cancer patients, the need for high precision analyses of circulating tumour-derived nucleic acid molecules is obvious, but not necessarily implemented.

One of the most commonly used platforms is droplet digital PCR (ddPCR), where the partitions are represented by thousands of nanolitre-scale droplets, formed by water-in-oil emulsion (Hindson et al., *Anal Chem* 2011, 83(22): 8604-8610), The sample partitioning inherent for ddPCR considerably reduces the competition from any background DNA, allowing detection of minimal amounts of a target of interest. The sensitivity is in principle only limited by the number of droplets analysed, and the method has been demonstrated to trace one mutated gene copy in the background of 200,000 wild-type molecules (Pekin et al. *Lab Chip* 2011, 11(13): 2156-2166). This makes ddPCR particularly valuable for analyses of various types of non-invasive biomarkers, such as detection of KRAS mutations in the blood of colorectal cancer patients, predicting lack of response to targeted treatment, screening for metastatic breast cancer by small increases in HER2 copy number in plasma samples, gene expression analyses to detect hepatocellular carcinoma from circulating tumour cells, and detection of bladder cancer among haematuria patients.

An abiding difficulty with absolute DNA quantification is the standardisation of results using suitable controls. This is a particular problem in methylation analyses. As noted above, absolute DNA quantification can be combined with methylation-specific FOR to quantify the proportion of a sample displaying a particular methylation patter. In particular, ddPCR technology has great potential for DNA methylation analysis, but few such studies have been published to date, Generation of consistent methylation data is dependent on the use of a suitable control for normalisation, but there is currently a lack of consensus regarding how to perform standardised experiments.

The inventors have developed a robust control for absolute DNA quantification, which has particular utility in ddPCR DNA methylation analyses. The value of the disclosed control in terms of increased precision of normalised methylation data is demonstrated in the Examples.

The inventors have identified four genes in particular as suitable controls for absolute quantification of a nucleic acid: SYT10, EPHA3, PLEKHF1 and KBTBD4. The inventors identified these four genes by testing a number of genes chosen based on close proximity to the centrosome of the chromosome on which each is located. A combination of these four genes was identified as a superior control to those currently used in the art, and in particular the new 4-gene control according to the present invention out-performed the previously reported ACTB and C-LESS single-gene controls currently used in dPCR analysis of methylated DNA. According to the present disclosure, at least two of the four genes are used in combination to provide a control for absolute DNA quantification. Use of the control provided by the inventors of the present application enables improved methods for absolute nucleic acid quantification, in particular improved absolute quantification of DNA methylation patterns.

The present invention is of particular use in DNA methylation analysis, most notably by digital PCR (for example ddPCR), but is not limited to such use and can be used in any method of absolute quantitation of nucleic acids. The invention enables improved precision of target quantification, which is of particular importance in fields such as liquid biopsy, which has great potential for disease detection and monitoring, and in monitoring the emergence of drug resistance.

Thus in a first aspect, provided herein is a method of quantification of a target nucleic acid, wherein at least any two of the genes SYT10, EPHA3, PLEKHF1 and KBTBD4 are used as control genes, said method comprising:

(i) amplifying the target nucleic acid, or a target region thereof, to yield a target amplicon, wherein the amplification is performed using a quantitative amplification method which allows absolute quantification and which uses primers;

(ii) amplifying a target region of at least two of the control genes SYT10, EPHA3, PLEKHF1 and KBTBD4, to yield a control gene amplicon for each of the at least two control genes, wherein the amplification is performed using a quantitative amplification method which allows absolute quantification and which uses primers, wherein no more than one target region of any one of the control genes is amplified;

(iii) normalising the results of the target amplification of (i) using the results of the control amplification of the target regions of the at least two control genes of (ii); and (iv) based on (iii), determining a value for the amount of the target nucleic acid.

In another aspect, provided herein is a kit comprising one or more primer sets suitable for use in PCR to amplify a target region within a target gene to generate an amplicon, said one or more primer sets selected from a primer set comprising:

(i) a first primer and a second primer which bind within SYT10;

(ii) a first primer and a second primer which bind within EPHA3;

(iii) a first primer and a second primer which bind within PLEKHFI; and (iv) a first primer and a second primer which bind within KBTBD4;

wherein the first primer and the second primer of the one or more primer sets each binds a site within the target gene which does not contain any CpG dinucleotides.

The kit may comprise any two or any three of primer sets (i) to (iv). In one preferred embodiment the kit comprises the primer pairs of parts (i), (ii), (iii) and (iv).

In another aspect, provided herein is the use of an internal control in a method of amplification for absolute quantification of a target nucleic acid, wherein at least any two of the genes SYT10, EPHA3, PLEKHFI and KBTBD4 are used as control genes, and their use as control genes comprises a quantitative amplification of the gene or a target region thereof.

According to the quantitation method set out above, the target nucleic acid, or a region thereof, is amplified to yield a target amplicon. The target nucleic acid may be DNA or RNA. When the target nucleic acid is DNA, the DNA may be genomic DNA (gDNA), plasmid DNA, complementary DNA (cDNA) or any other form of DNA, The DNA may be of any length. When the target nucleic acid is RNA, prior to amplification the RNA is reverse transcribed into cDNA using the enzyme reverse transcriptase. The nucleic acid which is amplified is DNA, but by using reverse transcription an RNA molecule may nonetheless be quantified. The target nucleic acid may be single stranded or double stranded.

By "target" nucleic acid is simply meant a nucleic acid of interest, the concentration or amount of which it is desired to quantify. For instance the target nucleic acid may be gDNA or plasmid DNA, if the skilled person wishes to quantify the concentration of gDNA or plasmid DNA in a gDNA sample or a plasmid DNA sample, respectively, for instance during preparation of DNA for NGS. The target nucleic acid may be a particular mRNA, if for instance it is desired to quantify the level of expression of a gene of interest in a sample. As noted above, if the target nucleic acid is an RNA, it is reverse transcribed into cDNA before amplification. The target nucleic acid may be a particular allele or variant of a gene, if it is desired to quantify the amount of a given allele or variant in a biological sample. The target nucleic acid may be a DNA fragment demonstrating a particular methylation pattern, if it is desired to quantify the amount of a given methylation pattern in a biological sample. In this embodiment of the invention, in which a methylation pattern is quantified, the DNA fragment may in particular be a fragment of gDNA comprising CpG islands. The DNA fragment may in particular comprise a gene of interest or the promoter of a gene of interest.

In particular embodiments of the disclosure, the target nucleic acid is a gene (i.e. a target gene), a gene promoter (i.e. a promoter of a target gene) and/or a biomarker. A biomarker as defined herein is a nucleic acid molecule which may be used as an indicator for a particular biological condition, e.g. a disease. A biomarker may be a gene which is up- or down-regulated in a particular biological condition, and whose up- or down-regulation is indicative of that condition, or any DNA sequence which is altered in a particular condition. A biomarker may alternatively be a DNA modification which is indicative of a particular condition, e.g. methylation of a gene of interest or the promoter of a gene of interest. As is well known in the art, DNA methylation within genes or gene promoters causes down-regulation of gene expression. DNA is generally methylated at position 5 of cytosine residues within CpG dinucleotides (i.e. a pair of nucleotides in which a guanine nucleotide is located immediately 3' to a cytosine nucleotide).

The target nucleic acid may thus be detected, or quantified, in the context of detecting a condition, which may be any disease or disorder. The target nucleic acid may thus be DNA obtained from a subject under test, or investigation, and this may include DNA obtained from a sample of cells from the subject, e.g. from a tumour, or from any tissue or organ of the body, including from blood or from circulating tumour cells (CTC), and cell-free DNA (cfDNA), including foetal cfDNA obtained from a mother. CfDNA has recently become recognised as resource for biomarkers of cancer progression, treatment response and drug resistance. Aberrant DNA methylation, including but not only in cfDNA, is a recognised hall-mark of many cancers. Thus, a particular application of the present method is in the detection and monitoring of cancer and in the monitoring of cancer treatment. In other embodiments the target nucleic acid may be from a pathogen or any infectious organism (e.g. microorganism) and the method may have utility in the detection of an infection.

The target nucleic acid is comprised within a sample. By the term "sample" as used herein is meant a substance comprising one or more nucleic acids. Such a sample may be a solution, e.g. an aqueous solution, or a suspension (e.g. an aqueous suspension). Alternatively the sample may be a solid, e.g. a freeze-dried (i.e., lyophilised) sample. The entire sample may be used in the method of the disclosure, or only a part of it. The sample may be any sample of interest, e.g.

it may be a research sample (i.e. a nucleic acid sample produced during scientific research), or it may be a clinical sample or veterinary sample. By "clinical sample" is meant a sample isolated from a human; by "veterinary sample" is meant a sample isolated from a non-human animal. Suitable clinical or veterinary samples include any isolate which contains the target nucleic acid. This may include any sample obtained from a human or non-human animal subject which contains cells or cfDNA, but in particular such a sample may be a sample of blood, plasma (or other blood-derived product which may contain cells or DNA), saliva, urine, CSF, exudate, sputum or other respiratory material, or any other body fluid (i.e. the sample may be a liquid biopsy sample), or it may be any sample of tissue or cells, e.g. a tissue biopsy sample. A sample such as a human or veterinary sample, or any other sample, may be processed to isolate and purify DNA. Methods for DNA isolation are well known in the art. For instance a commercial kit may be used, e.g. a DNeasy Blood & Tissue Kit (Qiagen) may be used to isolate DNA from animal blood or tissue (including from human blood or tissue), or a standard method such as phenol/chloroform extraction may be used.

A skilled person working in the clinic or clinical laboratory is able to obtain a sample without difficulty, e.g., a blood sample may be obtained by taking blood from a subject using standard techniques (e.g. phlebotomy), A plasma sample may be obtained from a blood sample by e.g., centrifugation. A saliva sample or urine sample may be easily obtained by non-invasive methods. A biopsy sample may be a body fluid or tissue sample obtained from a subject. Such a sample may be obtained e.g. surgically or using a needle and syringe, as is well known to the skilled person.

According to the present disclosure, a method of quantification of the target nucleic acid is specifically a method of absolute quantification of the target nucleic acid. By absolute quantification is meant that the concentration or amount of the target nucleic acid in a sample of interest is determined (for instance in terms of copy number or a Molar concentration value, i.e. in absolute terms as a value for the actual amount of target present). This is in contrast to a method of relative quantification, in which only the relative amount of target nucleic acid, compared to a calibrator, is determined.

According to the method of the disclosure, the target nucleic acid, or a target region thereof, is amplified to yield a target amplicon. It is generally preferable that only a region within a target nucleic acid is amplified, though in some embodiments the entire target nucleic acid may be amplified. The amplified DNA sequence may be of any length, though it is generally preferred when amplifying a DNA sequence that the amplified sequence is reasonably short, as generally a short DNA sequence is amplified more efficiently than a longer one. The region of DNA amplified may preferably be at least 50 base pairs (bp) long, for instance at least 75, 100, 125 or 150 bp long. There is no particular maximum length of the region of DNA amplified, but in certain embodiments it may be at most 800, 700, 600, 500, 400, 300, 250 or 200 bp. The target region may be a region of particular interest within the target nucleic acid; alternatively the target region may be selected based on it sequence, e.g., a sequence which is particularly suitable or convenient for amplification may be selected. The target region may be selected at random within the target nucleic acid. The skilled person is well able to design an amplification reaction, including if necessary selecting a suitable target region within the target nucleic acid, Amplification of the target sequence (be that the target nucleic acid or a target region thereof) yields a target amplicon. By amplicon as defined herein is meant the amplification product. The target amplicon is the product of the amplification of the target nucleic acid or target region thereof.

The amplification of the target region is performed using a quantitative amplification method which allows absolute quantification and uses primers. As mentioned above, in the field of nucleic acid analysis, methods for the quantification of a target nucleic acid provide either absolute or relative quantification of the target.

Relative quantification allows comparison of the level of a target nucleic acid in two or more different samples, and/or the levels of two or more target nucleic acids in a single sample. Relative quantification of target nucleic acids may be used in differential expression analyses to analyse the difference in expression of a gene of interest between samples, or two genes of interest within a sample. Relative quantification is straightforward and entails comparison of the amount of a target nucleic acid in a sample to that of one or more internal controls. Differences in the amounts of target nucleic acids can thus be determined based on their relative levels compared to a control gene, often a housekeeping gene. Relative quantification thus allows relative differences between the amounts of target nucleic acids in a sample to be identified, e.g. changes in gene expression may be identified and quantified using relative quantification of nucleic acids. However, such methods do not allow the absolute determination of how much of a target is present in a sample. Relative quantification of a target nucleic acid is generally performed using qPCR.

Absolute quantification of a target nucleic acid enables the precise determination of the number of target nucleic acid molecules within a sample, e.g. in terms of copy number or concentration. The two most common methods for performing absolute quantification of a target nucleic acid are absolute quantification gPCR and digital PCR, though any method which allows absolute quantification of a target nucleic acid in a sample and uses primers may be used in the method disclosed herein.

In absolute quantification qPCR, a calibration curve is generated using standards of known DNA concentrations. By comparing the result of amplification of a target nucleic acid sequence in a sample of interest to the calibration curve, the DNA concentration of the sample of interest may be determined.

Digital PCR is performed by separating a PCR reaction mix into a large number of partitions. The reaction is performed individually in each partition. At the end of the reaction, a binary result is obtained from each partition: a product is detected or is not detected, thus determining whether a target nucleic acid molecule was or was not present in the partition. The proportion of partitions in which a product was detected is calculated, and based on this statistical analysis is performed to estimate the average number of target molecules which were present in each partition at the beginning of the reaction, and allows the precise quantification of the number of target nucleic acid molecules in the sample of interest. The Poisson distribution is generally used for the statistical analysis.

Detection of a product in any of the methods of DNA quantitation described above is generally performed using fluorescent substrates, Detection may be performed using a fluorescent dye which only fluoresces when bound to DNA, e.g. SYBR® Green (Thermo Fisher Scientific, USA). Alternatively, detection may be performed using a nucleic acid probe which binds the DNA sequence amplified by the amplification reaction (i.e. a probe which binds the amplicon) and comprises a fluorophore at one end and a fluorescence quencher at the other. When the probe is intact, the close proximity of the fluorophore and the fluorescence quencher prevents detectable fluorescence from the fluorophore. During amplification using a DNA polymerase, the probe binds the amplicon and is cleaved during the extension step by the 5'-3' exonuclease activity of the DNA polymerase. This leads to separation of the fluorophore and the fluorescence quencher, and consequently the detection of fluorescence from the fluorophore. A probe as described may be known in the art as a TaqMan probe.

Using these methods, the amount of fluorescence detectable (i.e. the fluorescence intensity) is proportionate to the yield of amplification product (i.e. a doubling in the amount of amplification product corresponds to a doubling in fluorescence intensity). In qPCR, the fluorescence intensity is used to calculate the amount of DNA present in a sample, based on a calibration curve. In dPCR on the other hand, a fluorescence threshold is determined based on the fluorescence amplitudes of the partitions. This threshold corresponds to the presence or absence of a product in any given partition (i.e., a partition with a fluorescence intensity higher than the threshold is considered to contain an amplification product; a partition with a fluorescence intensity lower than the threshold is considered not to contain an amplification product), As mentioned, although the above-described techniques are the most common techniques for absolute quantification of a DNA molecule in a sample, any technique which allows absolute quantification of a DNA molecule in a sample and uses primers may be used in the method disclosed herein.

Further, although it is preferred to use a fluorescence-based method such as is described above to detect and quantify the amplicons, this is not essential and any method of detecting the target and control amplicons in steps (i) and (ii) of the method may be used. Thus, steps (i) and (ii) may more particularly be defined as comprising quantification of the amount of target amplicon and control gene amplicon, respectively.

As is known to the skilled person, a primer is a short, single-stranded nucleic acid molecule used to prime DNA amplification in DNA polymerase-based methods of DNA amplification. Thus the amplification method used in the method disclosed herein utilises a DNA polymerase. As is known to the skilled person, DNA polymerases are unable to initiate de novo DNA synthesis; rather they are only able to add nucleotides to the 3' end of an existing nucleic acid strand, and hence a primer is used to prime amplification: the DNA polymerase extends the primer to yield a newly-synthesised DNA strand. Any individual DNA amplification reaction requires two primers. In molecular biology methods of DNA amplification, primers are used to define the boundaries of the amplified region. A primer may in particular be a single-stranded DNA molecule. A primer may be between 15 and 40 nucleotides long, for instance a primer may be at most 40, 35, 30, 25, 22 or 20 nucleotides long, and/or at least 15, 18 or 20 nucleotides long. The skilled person is well able to design suitable primers for use in amplification of a target nucleic acid or target region thereof. Such primer design may be performed manually or using a computer programme designed for the purpose (e.g. Primer Express, Thermo Fisher Scientific), The DNA polymerase used for DNA amplification may be any suitable DNA polymerase. The DNA polymerase may be a thermostable DNA polymerase, by which is meant a DNA polymerase which is stable at temperatures up to e.g. 80, 85, 90 or 95° C. Suitable DNA polymerases include Taq polymerase from Thermus aquaticus and KOD polymerase from Thermococcus kodakaraensis. Suitable DNA polymerases are known to the skilled person and are widely commercially available, and may be selected based on the method of DNA amplification chosen. The DNA polymerase may have a 3'-5' exonuclease activity.

As noted above, the technique used to amplify the target nucleic acid, or target region thereof, may be any suitable technique known in the art. In a preferred embodiment the technique (i.e. the quantitative amplification method) may comprise a PCR reaction. For instance, as noted above, the quantitative amplification method may be absolute quantitation qPCR or digital PCR. A PCR reaction (including digital PCR or absolute quantitation qPCR) may be performed in a thermocyclerA non-PCR based method may alternatively be used, for instance an isothermal method such as loop-mediated isothermal amplification (LAMP), nucleic acid sequence-based amplification (NASBA) or strand displacement amplification (SDA) may be used.

The method disclosed herein further comprises amplifying a target region of at least two of the control genes SYT10, EPHA3, PLEKHF1 and KBTBD4. By control gene is meant a gene which is used as a control for absolute quantification of the target nucleic acid, i.e. amplification of the control gene is used to normalise the results of the amplification of the target nucleic acid. At least two of the genes SYT10, EPHA3, PLEKHF1 and KBTBD4 are used as control genes. SYT10 encodes the $Ca^{2+}$+sensor Synaptotagmin-10. The human SYT10 gene is located on chromosome 12, and in the Homo sapiens hg38 genome assembly is located at coordinates 33376830-33439522. EPHA3 encodes the protein-tyrosine kinase ephrin type-A receptor 3 (EPH receptor A3). The human EPHA3 gene is located on chromosome 3, and in the hg38 genome assembly is located at coordinates 89107749-89479502. PLEKHF1 encodes Pleckstrin homology domain-containing family F member 1, the function of which is not certain. The human PLEKHFI gene is located on chromosome 19, and in the hg38 genome assembly is located at coordinates 29665420-29675476. KBTBD4 encodes Kelch repeat and BTB domain-containing protein 4, the function of which is not certain. The human KBTBD4 gene is located on chromosome 11, and in the hg38 genome assembly is located at coordinates 47572197-47579015. The four control genes may be identified in the genomes of non-human species based on sequence homology to the human genes.

The at least two of the control gens used as a control for absolute quantification of the target nucleic acid may include SYT10 and EPHA3; SYT10 and PLEKHF1; SYT10 and KBTBD4; EPHA3 and PLEKHFI; EPHA3 and KBTBD4; or PLEKHF1 and KBTBD4.

As discussed above, in the method of the disclosure, the target nucleic acid is comprised within a sample. The sample comprising the target nucleic acid further comprises nucleic acids (preferably DNA) comprising the at least two control genes. In other words, the control genes are genes which are present in the sample (i.e. are endogenous to the sample), or more particularly which are present together with the target nucleic acid in the nucleic acids which are contained in the sample. In order that the control genes are able to fulfill their purpose as controls, the target nucleic acid and the nucleic acids comprising the at least two control genes are isolated together.

In the method disclosed herein, a target region of at least two of the four above-mentioned control genes is amplified.

Any region of each control gene may be selected as a target region, and the skilled person is able to select a suitable sequence from within the target gene for amplification. The target region of a control gene may be located within an exon of the control gene or an intron of the control gene, or indeed the target region of a control gene may bridge a junction between an exon and an intron. The target region of a control gene which is amplified is preferably a similar length to the target nucleic acid, or target region thereof, which is amplified, i.e. the target region of the control gene may be no more than 300, 275, 250, 225, 200, 175 or 150 base pairs (bp) in length and/or at least 50, 75, 100, 125 or 150 bp long.

Amplification of the target region of a control gene yields a control gene amplicon. A control gene amplicon, as defined herein, is the product of amplification of the target region of the control gene.

In the method disclosed herein, a target region of at least two of the control genes SYT10; EPHA3; PLEKHF1 and KBTBD4 is amplified. In other words, in the method disclosed herein at least two of SYT10; EPHA3; PLEKHF1 and KBTBD4 may be selected for use as control genes. Any two of SYT10, EPHA3, PLEKHF1 and KBTBD4 may be selected for use as control genes in the method disclosed herein, or any 3 of SYT10, EPHA3, PLEKHF1 and KBTBD4 may be selected for use as control genes in the method disclosed herein. If any 3 of SYTIO, EPHA3, PLEKHF1 and KBTBD4 are selected for use as control genes, the selected combination may include SYT10, EPHA3 and KBTBD4; SYT10, PLEKHF1 and KBTBD4: EPHA3, KBTBD4 and PLEKHF1; or SYT10, EPHA3 and PLEKHF1. Alternatively, all four of SYT10, EPHA3, PLEKHF1 and KBTBD4 may be selected for use as control genes in the method disclosed herein. For each of the control genes selected for use in the method of the disclosure, a target region is selected and amplified. Only a single target region is amplified of each selected control gene (i.e. no more than one target region of each control gene is amplified).

As discussed above, the target region of each selected control gene may be any region within the gene. In a particular embodiment, when SYT10 is used as a control gene, a target region within exon 3 of SYT10 is amplified. The nucleotide sequence of exon 3 of the human SYT10 gene is set forth in SEQ ID NO: 17. Exon 3 of the human SYT10 gene is natively located within the sequence context set forth in SEQ ID NO: 77. In a more general embodiment, when SYT10 is used as a control gene, a target region within SEQ ID NO: 77 is amplified. In a particular embodiment, when EPHA3 is used as a control gene, a target region within exon 3 of EPHA3 is amplified. The nucleotide sequence of exon 3 of the human EPHA3 gene is set forth in SEQ ID NO: 18. Exon 3 of the human EPHA3 gene is natively located within the sequence context set forth in SEQ ID NO: 78. In a more general embodiment, when EPHA3 is used as a control gene, a target region within SEQ ID NO: 78 is amplified.

In a particular embodiment, when PLEKHF1 is used as a control gene, a target region within exon 2 of PLEKHFI is amplified. The nucleotide sequence of exon 2 of the human PLEKHF1 gene is set forth in SEQ ID NO: 19, though this sequence may vary in particular at position 909, which nucleotide may differ from that set forth in SEQ ID NO: 19 due to the presence of a common single nucleotide polymorphism (SNP) at this location. Exon 2 of the human PLEKHF1 gene is natively located within the sequence context set forth in SEQ ID NO: 79. In a more general embodiment, when PLEKHFI is used as a control gene, a target region within SEQ ID NO: 79 is amplified (taking account of the variability of the nucleotide located at position 909 of PLEKHF1 exon 2). In a particular embodiment, when KBTBD4 is used as a control gene, a target region within exon 4 of KBTBD4 is amplified. The nucleotide sequence of exon 4 of the human KBTBD4 gene is set forth in SEQ ID NO: 21. Exon 4 of the human KBTBD4 gene is natively located within the sequence context set forth in SEQ ID NO: 80. In a more general embodiment, when KBTBD4 is used as a control gene, a target region within SEQ ID NO: 80 is amplified.

Like the target nucleic acid, or target region thereof, the target region of each selected control gene is amplified using a quantitative amplification method which allows absolute quantification and which uses primers. Such quantitative amplification methods are described above. Any such amplification method may be used, but preferably the quantitative amplification method used is a method which comprises a PCR reaction, and more preferably qPCR or dPCR.

Preferably, the same quantitative amplification method is used to amplify the target region of each of the at least two selected control genes.

In a particular and preferred embodiment of the method disclosed herein, the quantitative amplification method used to amplify the target nucleic acid, or the target region thereof, is the same quantitative amplification method used to amplify the target region of each of the selected control genes. By "same" is meant that the same technique is used, e.g. digital PCR may be used for amplification of the target nucleic acid (or target region thereof) and for amplification of the target regions of each of the selected control genes. As defined herein, a methylation-specific version of a quantitative amplification method and a non-methylation-specific version of the same quantitative amplification method are defined as the same quantitative amplification method, e.g. methylation-specific digital PCR and non-methylation-specific digital PCR are defined herein as the same technique. It can thus be seen that the quantitative amplification method used in step (ii) may defined as the same, or as an analogous, method to that used in step (i). In other words, the quantitative amplification method used in step (ii) allows absolute quantification in the same manner as the quantitative amplification method used in step (i).

Methods by which amplification of a target sequence may be detected are discussed above. Any technique known in the art may be used to detect target sequence amplification in the method disclosed herein (as used herein, the term "target sequence" encompasses the target nucleic acid (or target region thereof) and the target regions of the at least two control genes). Target sequence amplification may be detected using fluorescence-based methods. For instance, target sequence amplification may be detected using a dye which fluoresces only when bound to DNA, such as SYBR Green. Alternatively, target sequence amplification may be detected using a fluorescent probe. As defined herein, a fluorescent probe is a nucleic acid probe which carries a fluorescent dye. Such a probe includes in particular TaqMan probes, which are described above. A fluorescent probe used in the method of the invention may be designed without difficulty by the skilled person, or using a computer programme which is able to design a fluorescent probe. A fluorescent probe as defined herein is a single-stranded nucleic acid molecule comprising a fluorophore and, preferably, a fluorescence quencher. Preferably, a fluorophore is located at one end of the probe and a fluorescence quencher at the other. For instance, the fluorophore may be located at the 5' end of the probe and the fluorescence quencher at the 3' end, or the fluorophore may be located at the 3' end of the probe and the fluorescence quencher at the 5' end. The fluorescent probe is preferably a single-stranded DNA molecule. The fluorescent probe may be at least 15, 18, 20, 22 or 25 nucleotides in length; the fluorescent probe may be at most 50, 45, 40, 35, 30, 28, 25 or 22 nucleotides in length. The skilled person is able to design a fluorescent probe without particular instruction, if necessary using a computer programme such as Primer Express. When a fluorescent probe is used to detect amplification of a target sequence, a DNA polymerase with a 3'-5' exonuclease activity is used for DNA amplification.

The fluorescent probe may comprise a minor groove binder (MGB), in particular an MGB may be covalently attached to the 3' end of the fluorescent probe. Probes comprising an MGB have been found to bind single-stranded DNA with improved stability relative to probes which do not comprise an MGB, and also have higher specificity for single base mismatches between the probe and its DNA target if the mismatch is located within the region of the DNA duplex formed from probe-target DNA binding to which the MGB binds.

The fluorophore of the fluorescent probe may be any fluorophore known in the art, in particular a fluorophore commonly used in fluorescent probes for detection of DNA amplification. Examples of such fluorophores are well known to the skilled person and include FAM (6-carboxyfluorescein), TET (tetrachlorofluorescein) and VIC®. The fluorescence quencher of the fluorescent probe may be any fluorescence quencher known in the art. It may be a non-fluorescent quencher or a weakly-fluorescent quencher. Appropriate quenchers used in the art are known to the skilled person and include TAMRA (tetramethylrhodamine), Black Hole Quencher (BHQ) and QSY®. The skilled person is able to design a probe for use in the method disclosed herein as a matter of routine.

Thus amplification of the target nucleic acid (or target region thereof) may be detected using a fluorescent probe, such as a TaqMan probe. In a particular embodiment the fluorescent probe specifically binds the target amplicon. A probe which specifically binds the target amplicon has a nucleotide sequence which is the reverse complement of part of one of the DNA strands in the amplicon. Alternatively seen, a probe which specifically binds the target amplicon has a nucleotide sequence which corresponds to part of one of the DNA strands in the amplicon. The fluorescent probe does not overlap either of the primer sequences used to generate the amplicon, but otherwise may bind the amplicon at any location. In this embodiment, amplification of the target nucleic acid, or the target region thereof, is performed in the presence of a fluorescent probe which specifically binds the target amplicon. By "in the presence of" as used herein is meant that the fluorescent probe is present within the amplification reaction mix in which the target sequence is amplified.

In another embodiment, one of the two primers used for amplification of the target nucleic acid (or target region thereof) comprises a 5' tail which is not complementary to the target nucleic acid or the target region thereof. By "5' tail" is meant a nucleotide sequence which is located at the 5' end of the primer, upstream of the region of the primer which binds the target sequence. The 5' tail of the primer is preferably not complementary to any sequence within the target nucleic acid or any sequence within a sample comprising the target nucleic acid. In this embodiment, the fluorescent probe specifically binds the 5' tail of the primer (i.e. the fluorescent probe has a nucleotide sequence which is the reverse complement of the 5' tail of the primer). A fluorescent probe which specifically binds the 5' tail of a primer binds only the 5' tail of the primer, i.e. its binding site does not extend into the region of the primer which binds the target nucleic acid (or target region thereof). In this embodiment, the amplification is performed in the presence of a fluorescent probe which specifically binds the 5' tail of a primer.

The amplification of the target regions of the at least two control genes may be detected using a fluorescent probe, such as a TaqMan probe. In a particular embodiment, amplification of a target region of a control gene may be detected using a fluorescent probe which binds the control gene amplicon. As detailed above, a fluorescent probe which specifically binds an amplicon has a nucleotide sequence which is the reverse complement of part of one of the DNA strands in the amplicon (alternatively seen as a nucleotide sequence which corresponds to part of one of the DNA strands in the amplicon), and may bind the amplicon at any location with the proviso that it does not overlap with either of the primer binding sites. According to the method of the disclosure, amplification of at least one of the target regions of the selected control genes may be detected using a probe which specifically binds the control gene amplicon. Accordingly, amplification of one or more of the target regions of the at least two control genes may be performed in the presence of a fluorescent probe which specifically binds the control gene amplicon.

In another embodiment, one of the primers used to amplify a target region of a control gene comprises a 5' tail which is not complementary to the target region of the control gene. The 5' tail of the primer is preferably not complementary to any sequence within the control gene or any sequence within a sample comprising the control gene. In this embodiment, the fluorescent probe specifically binds the 5' tail of the primer (i.e. the fluorescent probe has a nucleotide sequence which is the reverse complement of the 5' tail of the primer), and thus the amplification is performed in the presence of a fluorescent probe which specifically binds the 5' tail of a primer. Accordingly, in an embodiment, in the method of the disclosure one of the primers used to amplify the target region of one or more of the at least two control genes comprises a 5' tail which is not complementary to the target region, and the amplification is performed in the presence of a fluorescent probe which specifically binds the 5' tail.

It may be that the amplification of each target region of the selected control genes is detected using a fluorescent probe which binds the control gene amplicon, i.e. the amplification of each of the target regions of the at least two control genes may be performed in the presence of a fluorescent probe which specifically binds the control gene amplicon. Alternatively, amplification of each target region of the selected control genes may be performed using a primer pair of which one primer comprises a 5' tail which is not complementary to the target region of the control gene, in which case amplification of each target region of the selected control genes is detected using a fluorescent probe which binds the 5' tail.

It may be that amplification of at least one target region of the selected control genes is detected using a fluorescent probe which binds the control gene amplicon, and amplification of at least one of the selected control genes is detected using a fluorescent probe which binds to the 5' tail of a primer used for the amplification. Thus a combination of the two methods discussed above by which a fluorescent probe may be used to detect amplification of a DNA target may be used to detect amplification of the target regions of the at least two control genes used in the method disclosed herein.

Alternatively, the probes used for detecting the target and control gene amplicons may be provided with labels or reporter molecules other than fluorescent labels, by means of which they may be detected. Thus the probe may be labelled with a directly or indirectly detectable label, A directly detectable label is one that can be directly detected without the use of additional reagents, while an indirectly detectable label is one that is detectable by employing one or more additional reagents, e.g., where the label is a member of a signal producing system made up of two or more components. In many embodiments, the label is a directly detectable label, where directly detectable labels of interest include, but are not limited to colorimetric or other spectrophotometric labels, radioisotopic labels, chemiluminescent labels, and the like.

The amplification of each of the target regions of the at least two control genes may be performed separately, i.e. in separate reaction mixtures. That is, amplification of the target region of the first control gene may take place in a first reaction mixture and amplification of the target region of the second control gene may take place in a separate, second reaction mixture (and if present, amplification of the target region of the third control gene may take place in a separate, third reaction mixture and amplification of the target region of the fourth control gene may take place in a separate, fourth reaction mixture). Alternatively, and preferably, amplification of the target region of each of the selected at least two control genes may be performed simultaneously in the same reaction mixture. In this embodiment, the probes used to detect amplification of the target region of each control gene have different sequences; no probe is able to detect amplification of the target region of more than one target gene. In this embodiment each probe may comprise the same fluorophore, or may comprise a different fluorophore to enable amplification of the target region of each control gene to be distinguished. However, it is not essential that amplification of the target region of each control gene be distinguishable, particularly if the amplification method which allows absolute quantification used is digital PCR.

In a particular embodiment, amplification of the target nucleic acid (or target region thereof) and amplification of the target region of each of the at least two control genes is performed simultaneously in the same reaction mixture. In this embodiment, the probes used to detect amplification of each target sequence have different sequences (i.e. no probe can detect amplification of more than one target sequence). Each of the probes used to detect amplification of a target region of a control gene may comprise the same fluorophore (particularly when the amplification method which allows absolute quantification used is digital PCR). The probe used to detect amplification of the target nucleic acid (or target region thereof) comprises a different fluorophore to any of the probes used to detect amplification of a target region of a control gene. The fluorophore used to detect amplification of the target nucleic acid (or target region thereof) is a different molecule (i.e. has a different molecular structure) to the fluorophore(s) used to detect amplification of the target regions of the control genes, and also a different emission wavelength to the fluorophore(s) used to detect amplification of the target regions of the control genes, so that amplification of the target nucleic acid (or target region thereof) can be distinguished from amplification of the target regions of the control genes.

Amplification of the target nucleic acid, or a target region thereof, (the "target amplification") using a method which allows absolute quantification of the target provides a concentration or other value for the amount of the target nucleic acid. Amplification of the target regions of the at least two control genes (the "control amplification") using a method which allows absolute quantification of the controls provides a concentration or other value for the amount of the control. Following target amplification and control amplification, the results of the control amplification are used to normalise the results of the target amplification. In other words, the amount or concentration determined for the control genes is used to normalise the amount or concentration determined for the target nucleic add. The skilled person is able to normalise the results of the target amplification using standard techniques, Generally, normalisation of the results is performed by dividing the obtained concentration of the target gene by the obtained concentration of the control.

Based on the normalisation of the result of the target amplification, a value for the amount of the target nucleic acid is determined. This can be performed by multiplying the normalised values by a constant. The constant may be the mean concentration of the control across all experiments.

In a particular embodiment of the method disclosed herein, at least any 3 of the genes SYT10, EPHA3, PLEKHF1 and KBTBD4 are used as controls. In this embodiment, target regions of any three of the control genes are amplified to yield target amplicons, and normalisation of the results of the target amplification is performed using the results of the control amplification of the target regions of the at least three control genes.

In another embodiment of the method disclosed herein, each of the genes SYT10, EPHA3, PLEKHF1 and KBTBD4 are used as controls. In this embodiment, a target region of each of the four control genes is amplified to yield a target amplicon, and normalisation of the results of the target amplification is performed using the results of the control amplification of the target regions of each of the four control genes.

In a particular embodiment of the method disclosed herein, the target nucleic acid is a methylated DNA target, and the method comprises quantifying the amount of methylated target DNA in a sample comprising the target DNA. As described above, DNA methylation occurs at position 5 of cytosine residues within CpG dinucleotides, which yields 5-methylcytosine. Methylation of genes and gene promoters causes down-regulation of gene expression, and aberrant DNA methylation is frequently seen in cancer cells. DNA methylation analysis is thus a useful tool in cancer diagnosis and in the monitoring of cancer treatment.

As is known to the skilled person, in any mammalian cell some level of DNA methylation is seen, Thus this embodiment of the disclosed method is generally directed to analysing the level of DNA methylation in a particular target gene or gene promoter, which may be a biomarker. Quantifying the amount of methylated target DNA in a sample allows both the absolute quantification of the amount or concentration of methylated target DNA in the sample, and also the calculation of the proportion of target DNA in the sample which is methylated.

In a particular embodiment of the disclosed method, in which the target nucleic acid is a methylated DNA target, the method comprises:

(a) subjecting a sample comprising the target DNA to bisulphite conversion;

(b) amplifying the target DNA, or a target region thereof, to yield a target amplicon, wherein the amplification is performed using a quantitative amplification method which allows absolute quantification and which uses primers;

(c) amplifying a target region of at least two of the control genes SYT10, EPHA3, PLEKHF1 and KBTBD4 to yield a control gene amplicon for each of the at least two control genes, wherein the amplification is performed using the same quantitative amplification method as used in (b), and wherein no more than one target region of any one of the control genes is amplified; and (d) normalising the results of the target amplification of (b) using the results of the control amplification of the target regions of the at least two control genes of (c); and (e) based on (d), determining a value for the amount of the methylated target DNA.

Bisulphite conversion is a technique commonly used in DNA methylation analysis, as will be known to the skilled person. In bisulphite conversion, DNA is treated with (i.e. contacted with) bisulphite, e.g., sodium bisulphite, which has the formula $NaHSO_3$. Bisulphite is readily commercially available, including in kits provided specifically for bisulphite conversion of DNA (e.g. EpiTect Bisulfite Kit, Qiagen). Bisulphite converts cytosine residues to uracil, but leaves 5-methylcytosine unaltered. Bisulphite treatment of DNA thus selectively alters unmethylated cytosine, enabling the identification of methylated cytosine nucleotides within a sequence, ag, by sequencing or methylation-specific amplification of a sequence of interest. The skilled person is able to carry out bisulphite treatment of DNA without particular instruction, if necessary by using a bisulphite fit as described above and following the manufacturer's instructions.

Amplification of the target DNA (or target region thereof) is performed as described above. Similarly, amplification of the target regions of the at least two control genes selected is performed as described above. As stated, the amplification of the target regions of the at least two control genes is performed using the same quantitative amplification method as is used to amplify the target DNA (or target region thereof). The term "same quantitative amplification method" is defined above.

Step (i) of the method may be further be defined as comprising determining the amount of methylated target DNA, or the amount of target amplicon arising or derived from methylated DNA.

Normalisation of the results of the target amplification using the results of the control amplification is described above, as is the use of the results of the normalisation to determine a value for the amount of target DNA.

In a preferred embodiment, when the target nucleic acid is a methylated DNA target, the amplification of the methylated DNA target is or comprises a methylation detection assay, for example methylation-specific PCR, as described in Eads et al. (*Nucleic Acids Res*, 28(8) e32, 2000) or another method of bisulphite sequencing. In methylation-specific PCR, DNA is first treated with bisulphite. The sequence of interest is then amplified by PCR using methylation-specific primers. Methylation-specific primers are primers which bind at a site comprising one or more CpG dinucleotides. The sequence of such a site varies following bisulphite treatment, depending on the methylation status of the CpG dinucleotide(s). A methylation-specific primer is complementary to the native DNA sequence of its binding site, i.e. it does not bind its binding site if the cytosine nucleotides in the CpG dinucleotide(s) have been converted to uracil by bisulphite treatment. Thus methylation-specific primers bind to their binding site in bisulphite-treated DNA only when the CpG dinucleotide(s) is/are methylated, and hence the bisulphite treatment has not altered the sequence of the binding site. This means that only amplification of methylated target takes place, allowing discrimination between methylated and unmethylated target DNA to take place at the level of amplification.

Alternatively, other methods of bisulphite sequencing may involve discrimination of the sequence variants resulting from bisulphite treatment after the amplification (e.g. PCR) step. Methods for this are known in the art. For example, methylation analysis by PCR may be performed using a methylation-specific fluorescent probe. A methylation-specific fluorescent probe binds the amplicon of a PCR reaction at a sequence which comprises CpG dinucleotides. The methylation-specific probe is complementary to the native DNA sequence of its binding site, i.e. if the cytosine nucleotides in the CpG dinucleotide(s) in the target DNA have been converted to uracil by bisulphite treatment, the methylation-specific probe will not bind the amplicon. Thus the methylation-specific probe will bind the amplicon only if the CpG dinucleotides in its binding site are methylated in the target DNA. This allows discrimination between methylated and unmethylated DNA to take place at the level of amplification detection. In such a case, the primers used in the PCR amplification step may be primers that are not methylation-specific. Such primers do not cover any CpG dinucleotides present in the original (non-bisulphite-treated) target DNA; in this case all the sequence variants which may have arisen due to DNA methylation in the region located between the two primers (including various patterns thereof) are amplified simultaneously. The different sequence (i.e. methylation) variants are then detected, or discriminated by the use of the methylation-specific probe to detect methylated target DNA.

Methylation analysis may be performed by PCR using only methylation-specific primers (i.e. only the primers are methylation-specific), only a methylation-specific probe (i.e. only the fluorescent probe is methylation-specific) or using methylation-specific primers and a methylation-specific probe.

In the method of the disclosure, amplification of the methylated DNA target by methylation-specific PCR may be performed using only methylation-specific primers; amplification of the methylated DNA target by PCR-based methylation analysis may alternatively be performed using only a methylation-specific probe (for detection of amplification), or using methylation-specific primers and a methylation-specific probe. In a preferred embodiment, the methylation-specific PCR is performed using methylation-specific primers, such that the methylated DNA target (or target region thereof) is only amplified when the cytosines in the CpG dinucleotides within the primer binding sites are methylated. When amplification of the methylated DNA target is performed using methylation-specific primers, amplification of the target is preferably detected using a fluorescent probe which specifically binds the target amplicon, most preferably using a methylation-specific probe which specifically binds the target amplicon, i.e. a fluorescent probe which binds the target amplicon in a methylation-specific manner (i.e. a fluorescent probe which only binds the target amplicon when the cytosine nucleotides in the target amplicon are methylated in the target DNA). Using a methylation-specific probe, only amplification of methylated target DNA is detected.

When the amplification of the methylated DNA target is performed using methylation-specific PCR, the amplification of the target regions of the at least two control genes is performed using primers which bind the control gene at sites which do not contain any CpG dinucleotides. In other words, in the amplification of a target region of each control gene, both primers bind the control gene at a sequence which comprises no CpG dinucleotides. By "a sequence which comprises no CpG dinucleotides" is more specifically meant a sequence which comprises no cytosine nucleotides which are located within a CpG dinucleotide, i.e. if a primer used to amplify a target region of a control gene binds the control gene at a sequence which comprises no CpG dinucleotides, it contains no full CpG dinucleotides and its 3' nucleotide does not make a single nucleotide overlap with a CpG dinucleotide. This means that amplification of the target regions of the at least two control genes is not methylation-specific following bisulphite treatment of the sample comprising the control genes.

Amplification of the target regions of the at least two control genes may be detected using a fluorescent probe, as discussed above. When target amplification is performed methylation-specific PCR, amplification of each target region of the at least two control genes may be detected using a fluorescent probe which specifically binds the control gene amplicon at a sequence which does not contain any CpG dinucleotides. This means that detection of control gene amplification is not methylation-specific following bisulphite treatment of the sample comprising the control genes, and the methylation status of the control gene does not influence detection of amplification of the control gene target region. By performing and detecting amplification of the target regions of the control genes in a non-methylation-specific manner, the control genes may be used as positive controls for the methylation-specific amplification of the target DNA, confirming the presence of intact DNA within the sample.

In a particular embodiment of the disclosed method, the sample comprising the target nucleic acid and nucleic acids comprising the at least two control genes is subjected to bisulphite treatment, and the target nucleic acid (or target region thereof) is amplified by methylation-specific PCR using methylation-specific primers. Target amplification is detected using a fluorescent probe which specifically binds the target amplicon, preferably wherein binding of the fluorescent probe to the target amplicon is also methylation-specific. Amplification of the target regions of the at least two control genes is performed by non-methylation-specific FOR, i.e., by FOR using primers which bind the control genes at sites (i.e. sequences) which do not contain any CpG dinucleotides, and amplification of each target region is detected using a fluorescent probe which specifically binds the control gene amplicon at a site (i.e. sequence) which does not contain any CpG dinucleotides. Amplification of the target nucleic acid (or target region thereof) and amplification of the target regions of the at least two control genes are performed simultaneously in the same reaction mixture.

As noted above, in the method of the disclosure, the method used for DNA amplification (target amplification and control amplification) may be any quantitative amplification method which allows absolute quantification and uses primers. In a particular embodiment of the invention, the quantitative amplification method used is digital PCR, Digital PCR is described above and is well known in the art. The skilled person is able to perform a digital PCR reaction without particular instruction. Examples of methods by which digital FOR may be performed include partitioning of a sample into microwells (as described in Morrison et al., 2006, *Nucleic Acids Res* 34: e123) or microfluidic chambers (as described in Ottesen et al., 2006, *Science* 314: 1464-1467). Each partition may be of approximately 1 nl volume. The DNA-containing sample may be diluted prior to partitioning to ensure the partitions are not saturated (i.e. that not every partition contains target DNA), since the concentration of the sample cannot be quantified if the partitions are saturated. Another dPCR method which may be used is BEAMING, which is based on emulsion PCR and in which templates are clonally amplified in the presence of beads.

The method of digital PCR employed in the method of the disclosure may in particular be droplet digital PCR. As described above, in droplet digital PCR the partitions take the form of water droplets in a water-in-oil emulsion. An optimal droplet size may be about 1 nl, Droplet digital FOR is described in Hindson et al, (supra), which includes teaching for droplet digital FOR performance. In droplet digital FOR, an aqueous sample comprising target DNA and PCR reagents (e.g. primers, DNA polymerase, buffer and dNTPS, and, if required, one or more fluorescent probes) is combined with a suitable oil to form a water-in-oil emulsion, using e.g. a droplet generator (e.g. a QX200 Droplet Generator (BioRad, USA)), The suitable oil may comprise stabilising surfactants. An example of an oil which may be used in droplet digital PCR is Bio-Rad Droplet Generation Oil.

Surfactant-stabilised droplets separate from the oil due to density differences, enabling transfer of the droplets to a container suitable for PCR, e.g. PCR tubes or more particularly a FOR plate. PCR is performed using standard techniques and DNA amplification detected by fluorescence, e.g. using a fluorescent probe as described above. Fluorescence may be detected using e.g. a droplet reader, in which a spacer fluid is used to separate and align the droplets for fluorescence detection. An example of a suitable droplet reader is the Bio-Rad QX200 Droplet Reader, with which Bio-Rad ddPCR Droplet Reader Oil may be used as the spacer fluid. Based on a calculated fluorescence threshold, each particle is assigned as positive (DNA amplification has taken place) or negative (DNA amplification has not taken place). The fluorescence threshold may be calculated using an appropriate algorithm, e.g. the threshold may be calculated using QuantaSoft (Bio-Rad). Data may be analysed using appropriate software, e.g. QuantaSoft.

In a particular embodiment of the disclosure, the disclosed method utilises methylation-specific droplet digital PCR for target amplification, and non-methylation-specific droplet digital PCR for control amplification, In another embodiment of the invention, the absolute quantification method used is absolute quantification qPCR. Absolute quantification qPCR is described above and is well known in the art. The skilled person is able to perform absolute quantification qPCR without particular instruction.

The target DNA amplified in the method of the disclosure may be obtained from any source which also contains at least two of the control genes SYT10, EPHA3, PLEKHF1 and KBTBD4. The source may be an animal, in particular a mammal. In a preferred embodiment, the target DNA is human (and thus the control genes are also human). Human target DNA may e.g. be derived from a clinical sample (as described above), or extracted from a human cell line.

As discussed above, in a particular embodiment of the disclosure, when SYT10 is used as a control gene, the target region is located within exon 3 of SYT10. When the target DNA is human, this target region may have (i.e., consist of) the nucleotide sequence set forth in SEQ ID NO: 13. This target region may be amplified using a first primer comprising or consisting of the nucleotide sequence set forth in SEQ ID NO: 1 and a second primer comprising or consisting of the nucleotide sequence set forth in SEQ ID NO: 2. Amplification of this target region may be detected using a fluorescent probe comprising the nucleotide sequence set forth in SEQ ID NO: 3. In particular, the probe may consist of the nucleotide sequence set forth in SEQ ID NO: 3, a fluorophore, a fluorescence quencher and, optionally, a minor groove binder. Amplification of the target region of SEQ ID NO: 13 may thus be performed in the presence of a fluorescent probe of SEQ ID NO: 3.

The nucleotide sequence set forth in SEQ ID NO: 13 is the native sequence of a target region located within SYT10, When SYT10 is fully methylated (i.e. methylated at all CpG dinucleotides) and the sample is bisulphite-treated prior to amplification of the target region (and unmethylated cytosine residues thus converted to uracil), the DNA sequence of SEQ ID NO: 13 is converted to that set forth in SEQ ID NO: 74. Amplification of SEQ ID NO: 74 yields an amplicon with the sequence set forth in SEQ ID NO: 70. Thus, if the sample is bisulphite-treated, the target region may comprise the sequence set forth in SEQ ID NO: 74. Amplification of the target region of SEQ ID NO: 74 may be performed in the same manner as amplification of the target region of SEQ ID NO: 13.

As discussed above, in a particular embodiment of the disclosure, when EPHA3 is used as a control gene, the target region is located within exon 3 of EPHA3. When the target DNA is human, this target region may have (i.e. consist of) the nucleotide sequence set forth in SEQ ID NO: 14. This target region may be amplified using a first primer comprising or consisting of the nucleotide sequence set forth in SEQ ID NO: 4 and a second primer comprising or consisting of the nucleotide sequence set forth in SEQ ID NO: 5. Amplification of this target region may be detected using a fluorescent probe comprising the nucleotide sequence set forth in SEQ ID NO: 6. In particular, the probe may consist of the nucleotide sequence set forth in SEQ ID NO: 6, a fluorophore, a fluorescence quencher and, optionally, a minor groove binder. Amplification of the target region of SEQ ID NO: 14 may thus be performed in the presence of a fluorescent probe of SEQ ID NO: 6.

The nucleotide sequence set forth in SEQ ID NO: 14 is the native sequence of a target region located within EPHA3. When EPHA3 is fully methylated (i.e. methylated at all CpG dinucleotides) and the sample is bisulphite-treated prior to amplification of the target region (and unmethylated cytosine residues thus converted to uracil), the DNA sequence of SEQ ID NO: 14 is converted to that set forth in SEQ ID NO: 75, Amplification of SEQ ID NO: 75 yields an amplicon with the sequence set forth in SEQ ID NO: 71. Thus, if the sample is bisulphite-treated, the target region may comprise the sequence set forth in SEQ ID NO: 75. Amplification of the target region of SEQ ID NO: 75 may be performed in the same manner as amplification of the target region of SEQ ID NO: 14.

As discussed above, in a particular embodiment of the disclosure, when PLEKHF1 is used as a control gene, the target region is located within exon 2 of PLEKHF1. When the target DNA is human, this target region may have (i.e. consist of) the nucleotide sequence set forth in SEQ ID NO: 15. This target region may be amplified using a first primer comprising or consisting of the nucleotide sequence set forth in SEQ ID NO: 7 and a second primer comprising or consisting of the nucleotide sequence set forth in SEQ ID NO: 8. Amplification of this target region may be detected using a fluorescent probe comprising the nucleotide sequence set forth in SEQ ID NO: 9. In particular, the probe may consist of the nucleotide sequence set forth in SEQ ID NO: 9, a fluorophore, a fluorescence quencher and, optionally, a minor groove binder. Amplification of the target region of SEQ ID NO: 15 may thus be performed in the presence of a fluorescent probe of SEQ ID NO: 9.

The nucleotide sequence set forth in SEQ ID NO: 15 is the native sequence of a target region located within PLEKHF1. When PLEKHF1 is fully methylated (i.e. methylated at all CpG dinucleotides) and the sample is bisulphite-treated prior to amplification of the target region (and unmethylated cytosine residues thus converted to uracil), the DNA sequence of SEQ ID NO: 15 is converted to that set forth in SEQ ID NO: 76. Amplification of SEQ ID NO: 76 yields an amplicon with the sequence set forth in SEQ ID NO: 72. Thus, if the sample is bisulphite-treated, the target region may comprise the sequence set forth in SEQ ID NO: 76. Amplification of the target region of SEQ ID NO: 76 may be performed in the same manner as amplification of the target region of SEQ ID NO: 15.

As discussed above, in a particular embodiment of the disclosure, when KBTBD4 is used as a control gene, the target region is located within exon 4 of KBTBD4. When the target DNA is human, this target region may have (i.e. consist of) the nucleotide sequence set forth in SEQ ID NO: 16. This target region may be amplified using a first primer comprising or consisting of the nucleotide sequence set forth in SEQ ID NO: 10 and a second primer comprising or consisting of the nucleotide sequence set forth in SEQ ID NO: 11. Amplification of this target region may be detected using a fluorescent probe comprising the nucleotide sequence set forth in SEQ ID NO: 12. In particular, the probe may consist of the nucleotide sequence set forth in SEQ ID NO: 12, a fluorophore, a fluorescence quencher and, optionally, a minor groove binder. Amplification of the target region of SEQ ID NO: 16 may thus be performed in the presence of a fluorescent probe of SEQ ID NO: 12.

The nucleotide sequence set forth in SEQ ID NO: 16 is the native sequence of a target region located within KBTBD4. When KBTBD4 is fully methylated (i.e. methylated at all CpG dinucleotides) and the sample is bisulphite-treated prior to amplification of the target region (and unmethylated cytosine residues thus converted to uracil), the DNA sequence of SEQ ID NO: 16 is converted to that set forth in SEQ ID NO: 20. Amplification of SEQ ID NO: 20 yields an amplicon with the sequence set forth in SEQ ID NO: 73. Thus, if the sample is bisulphite-treated, the target region may comprise the sequence set forth in SEQ ID NO: 20. Amplification of the target region of SEQ ID NO: 20 may be performed in the same manner as amplification of the target region of SEQ ID NO: 16.

When a primer as described above comprises the defined nucleotide sequence, the region of the primer which binds the control gene may consist of the defined sequence. The primer may comprise or consist of a target DNA-binding region, consisting of the defined nucleotide sequence, and a 5' tail region to which a fluorescent probe may bind.

In a particular and preferred embodiment of the disclosure, the disclosed method comprises:
  (a) subjecting a sample comprising the target DNA to bisulphite conversion;
  (b) amplifying the target DNA, or a target region thereof, to yield a target amplicon, wherein the amplification is performed by droplet digital PCR using methylation-specific primers and in the presence of a fluorescent probe, wherein:
    (i) the fluorescent probe specifically binds the target amplicon; or
    (ii) one of the primers used to amplify the target DNA, or target region thereof, comprises a 5' tail to which the fluorescent probe specifically binds;

(c) amplifying a target region of each of the control genes SYT10, EPHA3, PLEKHF1 and KBTBD4 to yield a control gene amplicon for each of the control genes, wherein the amplification is performed by droplet digital PCR using primers which bind the control genes at sites which do not contain any CpG dinucleotides, wherein no more than one target region of any one of the control genes is amplified, wherein the PCR amplification of the target regions of the control genes is performed simultaneously in the same reaction mixture as the methylation-specific PCR amplification of the target DNA of (b), and wherein the amplification of the single target regions of each of the control genes is performed in the presence of a fluorescent probe, wherein:

(I) each fluorescent probe specifically binds one of the control gene amplicons at a site which does not contain any CpG dinucleotides; or (II) one of the primers used to amplify the target region of each control gene comprises a 5' tail to which one of the fluorescent probes specifically binds; or (III) the probes are a mixture of probes as defined in (I) and probes as defined in (II);

(d) normalising the results of the target amplification of (b) using the results of the control amplification of the target regions of the control genes of (c); and (e) based on (d), determining a value for the amount of the methylated target DNA.

In a related aspect the disclosure provides the use of an internal control in a method of amplification for absolute quantification of a target nucleic acid, wherein at least any two of the genes SYT10, EPHA3, PLEKHF1 and KBTBD4 are used as control genes, and their use as control genes comprises a quantitative amplification of the gene or a target region thereof. The method of amplification for absolute quantification of a target nucleic acid and the quantitative amplification of the control gene, or target region thereof, may be performed as described above.

By "internal control" is meant a control which is within the absolute quantification method. Thus when amplification of a control gene (or target region thereof) is performed simultaneously in the same reaction mixture as amplification of the target nucleic acid (or target region thereof), the control gene can be considered an internal control.

In another aspect, the disclosure provides a kit comprising one or more primer sets suitable for use in PCR to amplify a target region within a target gene to generate an amplicon, said one or more primer sets selected from a primer set comprising:

(i) a first primer and a second primer which bind within SYT1O;

(ii) a first primer and a second primer which bind within EPHA3;

(iii) a first primer and a second primer which bind within PLEKHFI; and (iv) a first primer and a second primer which bind within KBTBD4;

wherein the first primer and the second primer of the one or more primer sets each binds a site within the target gene which does not contain any CpG dinucleotides;

preferably wherein the kit comprises the primer pairs of parts (i), (ii), (iii) and (iv).

Primers are described above. Each primer is a DNA molecule. One primer of one or more primer pairs may comprise a 5' tail to which a fluorescent probe may bind. The primer pairs may in particular bind within the human SYT10; EPHA3; PLEKHF1 and KBTBD4 genes, respectively.

The first and second primer of each primer pair may be provided together (i.e. in combination) or separately. When the primers of each primer pair are provided together, each primer pair of the kit may be provided together or separately. The primers may be provided in any suitable container, e.g. a tube. The primers may be provided in any suitable form, e.g. they may be provided in an aqueous solution or in lyophilised form. The primers may be provided at any concentration and in any amount or volume. If a primer is provided in an aqueous solution, the primer is preferably at a concentration higher than it will be used in a PCR reaction, e.g. 5 or 10 times higher, e.g. from 1 to 10 µM.

In a particular embodiment, the first primer and second primer which bind within SYT10 bind within exon 3 of SYT10. Such a first and second primer may amplify a DNA sequence with the nucleotide sequence set forth in SEQ ID NO: 13. A primer pair which can be used to amplify the nucleotide sequence set forth in SEQ ID NO: 13 may comprise a first primer comprising or consisting of the nucleotide sequence set forth in SEQ ID NO: 1 and a second primer comprising or consisting of the nucleotide sequence set forth in SEQ ID NO: 2.

In a particular embodiment, the first primer and second primer which bind within EPHA3 bind within exon 3 of EPHA3. Such a first and second primer may amplify a DNA sequence with the nucleotide sequence set forth in SEQ ID NO: 14. A primer pair which can be used to amplify the nucleotide sequence set forth in SEQ ID NO: 14 may comprise a first primer comprising or consisting of the nucleotide sequence set forth in SEQ ID NO: 4 and a second primer comprising or consisting of the nucleotide sequence set forth in SEQ ID NO: 5.

In a particular embodiment, the first primer and second primer which bind within PLEKHF1 bind within exon 2 of PLEKHF2. Such a first and second primer may amplify a DNA sequence with the nucleotide sequence set forth in SEQ ID NO: 15. A primer pair which can be used to amplify the nucleotide sequence set forth in SEQ ID NO: 15 may comprise a first primer comprising or consisting of the nucleotide sequence set forth in SEQ ID NO: 7 and a second primer comprising or consisting of the nucleotide sequence set forth in SEQ ID NO: 8.

In a particular embodiment, the first primer and second primer which bind within KBTBD4 bind within exon 4 of KBTBD4. Such a first and second primer may amplify a DNA sequence with the nucleotide sequence set forth in SEQ ID NO: 16. A primer pair which can be used to amplify the nucleotide sequence set forth in SEQ ID NO: 16 may comprise a first primer comprising or consisting of the nucleotide sequence set forth in SEQ ID NO: 10 and a second primer comprising or consisting of the nucleotide sequence set forth in SEQ ID NO: 11.

When a primer as described above comprises the defined nucleotide sequence, the region of the primer which binds the control gene may consist of the defined sequence. The primer may comprise or consist of a target DNA-binding region, consisting of the defined nucleotide sequence, and a 5' tail region to which a fluorescent probe may bind.

Each primer set may further comprise a fluorescent probe which binds the amplicon generated by PCR using the first primer and second primer of the primer set, wherein the fluorescent probe binds the amplicon at a site which does not contain any CpG dinucleotides. Such fluorescent probes are described above and may in particular consist of a nucleotide sequence which binds the amplicon at a site which does not contain any CpG dinucleotides, a fluorophore, a fluorescence quencher and, optionally, a minor groove binder.

In a particular embodiment, when the kit comprises a primer pair in which the first primer comprises or consists of the nucleotide sequence set forth in SEQ ID NO: 1 and the second primer comprises or consists of the nucleotide sequence set forth in SEQ ID NO: 2, the nucleotide sequence of the fluorescent probe may be that set forth in SEQ ID NO: 3.

In a particular embodiment, when the kit comprises a primer pair in which the first primer comprises or consists of the nucleotide sequence set forth in SEQ ID NO: 4 and the second primer comprises or consists of the nucleotide sequence set forth in SEQ ID NO: 5, the nucleotide sequence of the fluorescent probe may be that set forth in SEQ ID NO: 6.

In a particular embodiment, when the kit comprises a primer pair in which the first primer comprises or consists of the nucleotide sequence set forth in SEQ ID NO: 7 and the second primer comprises or consists of the nucleotide sequence set forth in SEQ ID NO: 8, the nucleotide sequence of the fluorescent probe may be that set forth in SEQ ID NO: 9.

In a particular embodiment, when the kit comprises a primer pair in which the first primer comprises or consists of the nucleotide sequence set forth in SEQ ID NO: 10 and the second primer comprises or consists of the nucleotide sequence set forth in SEQ ID NO: 11, the nucleotide sequence of the fluorescent probe may be that set forth in SEQ ID NO: 12.

The kit of the invention may further comprise reagents useful in DNA amplification, particularly in PCR, such as a DNA polymerase (e.g. Taq polymerase), a PCR buffer, and/or dNTPs. Magnesium ($Mg^{2+}$) is required for the function of many DNA polymerases; a PCR buffer may comprise magnesium, or magnesium may be provided separately, e.g. as a magnesium chloride ($MgCl_2$) solution. The kit of the invention may thus comprise a solution of $MgCl_2$. The kit may also comprise reagents useful in an absolute quantification method, e.g. dPCR. In particular, the kit may also comprise reagents useful in ddPCR, e.g. Droplet Generation Oil and/or Droplet Reader Oil.

As shown in the Examples herein, the control genes disclosed herein may be used to provide a robust control, preferably an internal control, for use in absolute nucleic acid quantification assays, particularly for methylation analysis or detection. The controls have a number of advantages and have been shown to perform better than the controls presently in use for dPCR. The control according to the present disclosure helps standardize the results by reducing unwanted variability in the end results, correcting for variable input amounts in the methods, and/or serving as loading controls for the amount of template. Thus, in addition to reducing the overall variability in the results of the method (e.g. in methylation values) and improving reproducibility, the control can adjust for unforeseen variations in the experimental pipeline.

The present invention may be more fully understood from the non-limiting Examples below and in reference to the drawings, in which:

The patent or application file contains at least one drawing executed in color. Copies of this patent or patent application publication with color drawing(s) will be provided by the Office upon request and payment of the necessary fee.

FIG. 1 shows that droplet dPCR amplification of a non-CpG containing sequence shared by members of a gene family as a control (approach A) provides poor results.

(A) Amplification of the ALDOA (Aldolase A family) assay results in a concentration of 425 copies/µl (threshold automatically determined by QuantaSoft), which is lower than expected based on the input amount and the number of targeted loci in the genome.

(B) Amplification of the CYCS (Cytochrome C family) assay results in lack of a positive droplet band.

FIG. 2 shows droplet dPCR amplification plots for individual and combined control assays.

(A) Individual amplification patterns for SYT10, EPHA3, PLEKHF1 and KBTBD4 comprising the 4Plex. Negative droplets are concentrated at the baseline amplitudes; positive droplets are present only in the IVD columns labelled 'bisulf. conv.' and are located above the negative droplets.

(B) Fluorescence amplitude plots for the 4Plex in a representative cell line. The horizontal line within the graph represents the threshold, dichotomizing positive and negative droplets. Left plot: the amplitude value (y-axis) for individual droplets (x-axis) is depictured (positive droplets above the threshold, negative droplets below the threshold). Right plot: the frequency of droplets (y-axis) at each fluorescence amplitude value (x-axis) is shown. Positive droplets have an amplitude value to the right of the threshold (the vertical line within the graph), and negative droplets amplitude value to the left of the threshold.

(C) Fluorescence amplitude plots for an alternative control panel consisting of SYT10, EPHA3, ALDH1B1 and SAMSN1.

Abbreviations: IVD; in vitro methylated DNA, NTC; non-template control water).

FIG. 3 shows the results of individual amplifications of control assay candidates. Negative droplets are concentrated at the baseline amplitudes; positive droplets are present only in the IVD columns and are located above the negative droplets.

FIG. 4 demonstrates that the 4Plex shows a consistent amplification pattern across the cell line panel with V9P as an exception. X-axis: the fluorescence amplitude value of the 4Plex; Y-axis: the frequency of droplets at each fluorescence value. The vertical line within each graph represents the threshold, dichotomizing droplets into negative (amplitude value left of the threshold) and positive (amplitude value right of the threshold).

(A) A representative cell line (KM12).
(B) V9P.

FIG. 5 shows that the 4Plex has minor effects on the non-normalised concentrations of the target. Non-normalised concentrations in methylated copies/pi (y-axis) are shown for 34 colorectal cancer cell lines (x-axis) from analysis without a control (square data points), and with the 4Plex included in the reaction (diamond-shaped data points). (A) CDO1; (B) SEPT9. The red trace in the (A) graph represents the non-normalised concentrations of CDO1 in the singleplex experiment, and the blue trace represents the non-normalised CDO1 concentration in the 4Plex experiment. The red trace in the (B) graph represents the non-normalised concentrations of SEPT9 in the singleplex experiment, and the blue trace represents the non-normalised SEPT9 concentration in the 4Plex experiment.

FIG. 6 shows that non-normalised VIM concentrations are lower with a control assay included in the reaction. Non-normalised VIM concentrations are shown across the cell line panel for an experiment without an internal control, and from experiments including one of the three controls; 4Plex, ACTB, and C-LESS (see legend). The red trace in the graph represents the non-normalised VIM concentration in the singleplex experiment. The blue trace represents the non-normalised VIM concentration in the experiment with the 4Plex. The green trace represents the non-normalised VIM concentration in the experiment with ACTB. And the purple trace represents the non-normalized VIM concentration in the experiment with the C-LESS.

FIG. 7 shows that the 4Plex-normalised concentrations show lower variance than non-normalised concentrations. Results are shown for CDO1 in two different cell lines (SW48 and SW480). Each analysis includes 12 replicates.

FIG. 8 shows a lower variation in 4Plex-normalised target gene concentrations is seen in replicates of the same sample. Non-normalised and 4Plex-normalised concentrations of SEPT9 (upper panel) and VIM (lower panel) are shown for replicates of two different samples (SW48 and SW480). Each analysis includes 14 replicates.

FIG. 9 shows that The 4Plex corrects for variable template amount.

(A) The 4Plex concentration across the cell line panel. The horizontal black line at 800 copies/µl indicates the expected 4Plex concentration, based on input amount and number of loci targeted by the 4Plex control assay (n=4).

(B) Non-normalised (left-hand bar in each pair) and normalised (right-hand bar in each pair) CDO1 concentrations in methylated copies/µl are shown for the same cell lines as in (A).

FIG. 10 shows that the 4Plex acts as a template-loading control that prevents erroneous scoring of template-negative samples. Upper panel: amplification of VIM in a selection of cell lines. The horizontal line in each column is the threshold: droplets above the threshold are positive: droplets below the threshold are negative. Lower panel: amplification of the 4Plex in the same cell lines. (Again, the horizontal line in each column is the threshold: droplets above the threshold are positive; droplets below the threshold are negative.) Water is used as a no template control (NTC).

FIG. 11 shows that normalisation by the 4Plex reduces the effect of chromosomal aberrations. Normalised concentrations of CDO1 (upper panel), SEPT9 (middle panel), and VIM (lower panel) are shown for three different internal controls; 4Plex (left), ACTB (middle) and C-LESS (right). Cell lines are grouped according to the chromosomal aberration status of their respective controls (x-axis). *Significant at a 1% level. **Significant at a 5% level.

EXAMPLES

Example 1—The 4Plex

Figure 1:
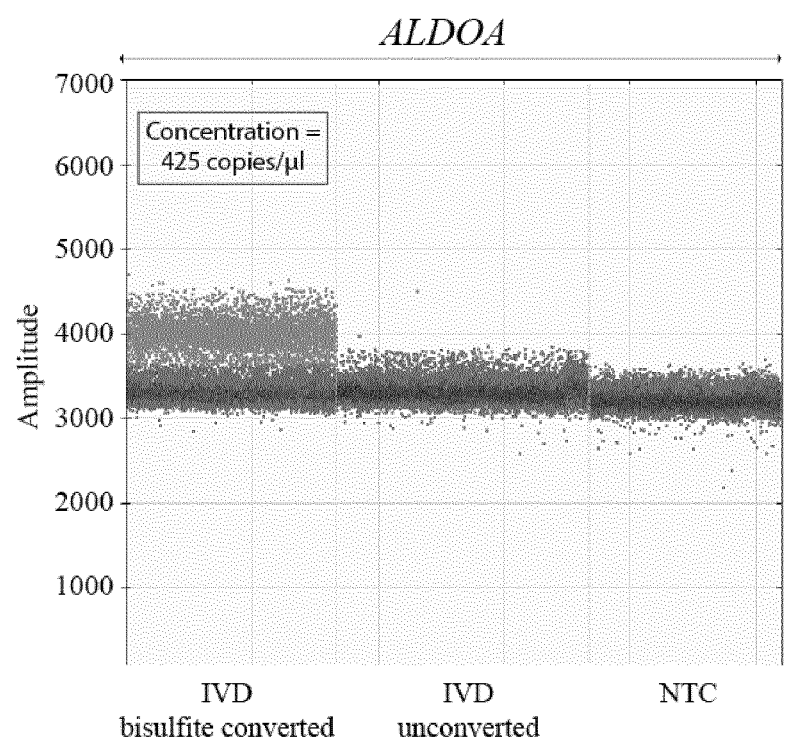
Figure 1:
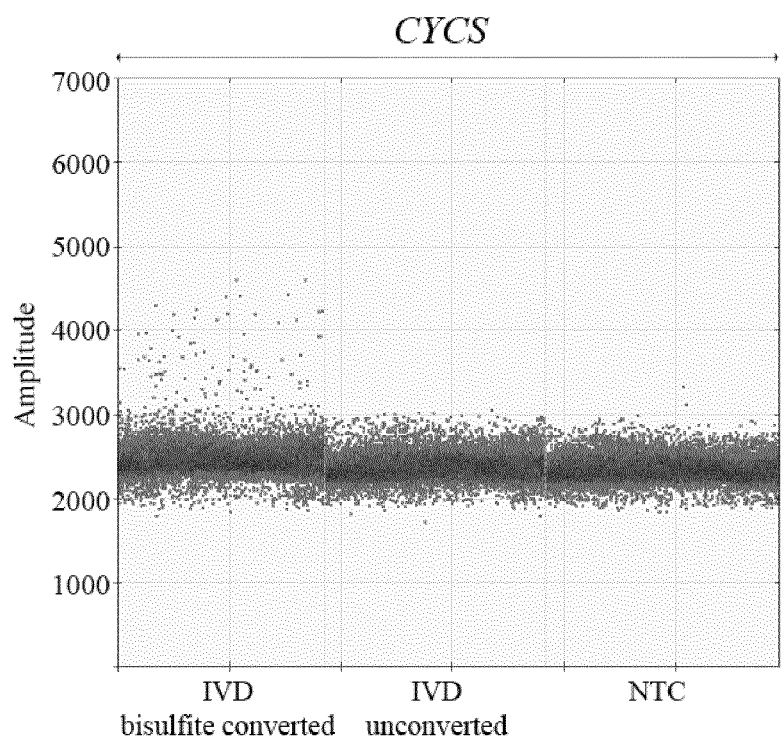

Materials and Methods
DNA from Cancer Cell Lines
DNA from 34 colorectal cancer cell lines (Caco2, CL-11, CL-34, CL-40, Co115, Colo205, Colo320, Colo678, DLD-1, EB, FRI, HCC2998, HCT116, HCT15, HT29, IS1, IS3, KM12, LoVo, LS1034, LS174T, NCI-H508, RKO, SW1116, SW1463, SW403, SW48, SW480, SW620, SW837, SW948, TC71, V9P, and WiDr) was isolated using either a standard phenol-chloroform protocol, or a magnetic beads approach (Maxwell® 16 System; Promega). DNA concentrations were measured using a NanoDrop 1000 Spectrophotometer (Thermo Fisher Scientific). Authentication of the cell lines was performed by short tandem repeat testing, as previously described (Ahmed et al., 2013, *Oncogenesis* 2:e71). DNA copy number data (Affymetrix Genome-Wide Human SNP 6.0 microarrays) were available for all cell lines (Berg et al., 2017, *Molecular Cancer* 16(1): 116).

Bisulfite Conversion
The EpiTect Bisulfite Kit (Qiagen) was used for bisulfite conversion of 1.3 µg DNA according to the manufacturer's standard protocol. After conversion in the MJ Mini Personal Thermal Cycler (Bio-Rad Laboratories), the samples were automatically purified and eluted in 40 µl elution buffer by the QIAcube System (Qiagen).

Design and Development of Candidate Internal Controls
With the aim of developing a control for methylation-specific ddPCR that targeted multiple non-CpG-containing loci located on different chromosomes, two approaches were tested. In the first approach, "A", a common sequence shared by several members of a gene family (the Aldolase A family; ALDOA, and the Cytochrome C family; CYCS was targeted. This approach implied introduction of only one control assay into the target gene reaction, with the rationale of reducing the chances of interference with target amplification. In the second approach, "B", multiple assays, targeting different loci in the exonic part of various genes located close to the centromeres (n=13; ALDH1B1, ANKRD30A, EPHA3, HAO2. IGFBPL1, ITGAD, KBTBD4, MRPS5, NIPA2, PLEKHF, SAMSN1, SYT10 and TTC5), were designed, and tested in different combinations. This approach implied introduction of several control assays into the target gene reaction. See Table 1 for assay sequences and their chromosomal locations. The best-performing control (VIC-labeled) was tested in combination with assays measuring the methylation of CDO1, SEPT9 and OM (FAM-labeled), through ddPCR analyses of 34 colorectal cancer cell lines. Finally, the performance of the control was compared to two previously published controls, ACTB (Eads et al., 2000, *Nucleic Acids Res* 28(8): E32) and C-LESS Weisenberger et al., 2008, *Nucleic Acids Res* 36(14): 4689-4698).

Droplet Digital PCR
The QX200™ Droplet Digital™ PCR System (Bio-Rad) was used for analyses. The ddPCR reaction mixture consisted of 1× ddPCR Supermix for Probes (Bio-Rad), 900 nM of each primer, 250 nM of the probe, and approximately 30 ng bisulfite-converted DNA template, in a final volume of 22 µl. Droplets were generated by the QX200 Droplet Generator (Bio-Rad), using 20 µl of the ddPCR mixture and 70 µl droplet generation oil (Bio-Rad). Samples were transferred to a 96-well PCR plate (Bio-Rad), and sealed in the PX1 PCR Plate Sealer (Bio-Rad). The PCR was performed in a T100 Thermal Cycler (Bio-Rad; see Table 2 for PCR cycling conditions). The fluorescence signals were measured by the QX200 Droplet Reader (Bio-Rad). For each experiment, the following control samples were included: two methylation-positive controls (commercially-available in vitro-methylated DNA; IVD; Zymo Research), one methylation-negative control (bisulfite-treated DNA from normal blood of healthy donors), one non-bisulfite-converted IVD sample, and a non-template control (NTC; water). All analyses were performed according to the digital MIQE-guidelines.

Data Analyses
Data from the QX200 Droplet Reader was analysed using QuantaSoft version 1.7.4.0917 (Bio-Rad). Based on the fraction of positive droplets, concentrations of methylated copies/μl were calculated by the software. Normalised concentrations were generated by dividing the concentration of the target gene by the concentration of the control. These normalised values were then multiplied by a constant, i.e. the mean concentration of the control among all analysed cell lines, in order to have them in the same range as the non-normalised concentration.

Statistics

Statistical analyses were performed using R version 3.2.2. In order to investigate how normalized concentrations were affected by chromosomal aberrations, cell lines were stratified according to the presence of deletions, gains, deletions and gains (both) or no aberration. Differences in mean among the groups were investigated using ANOVA.

Figure 2:
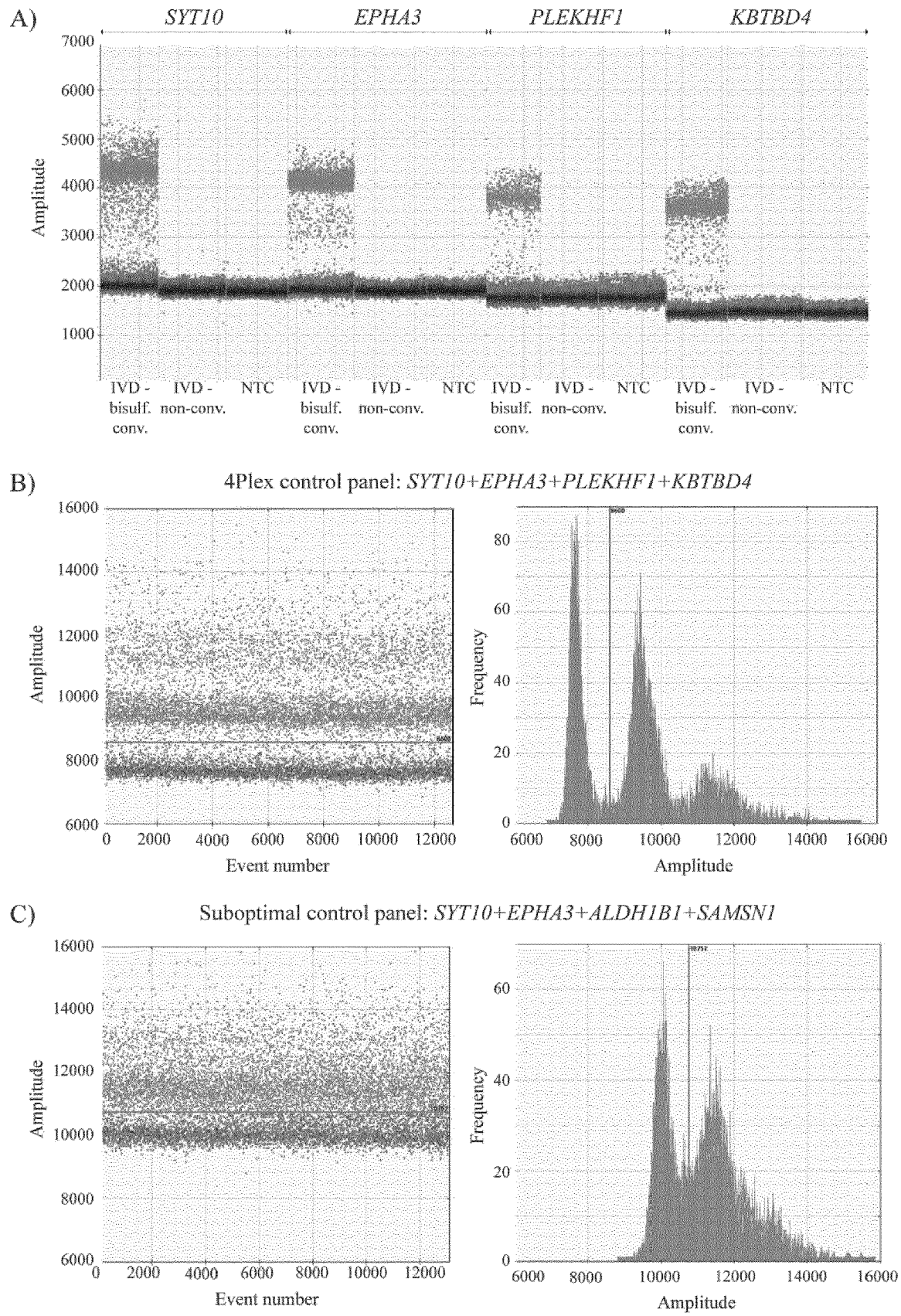
Figure 3:
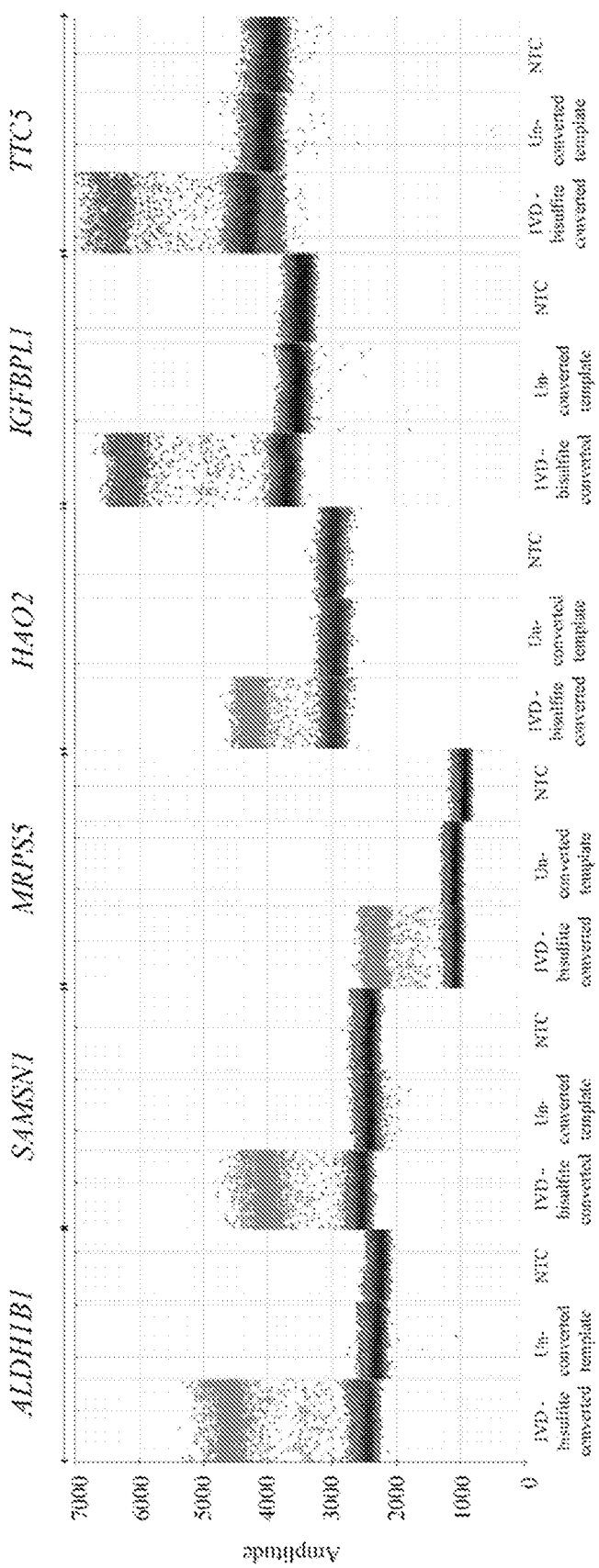

For the approach that combined single assays targeting different loci in the exonic part of various pericentromeric genes (approach B), nine (ALDH1B1, EPHA3, IGFBPL1, KBTBD4, MRPS5, PLEKHF1, SAMSN1, SYT10 and TTC5) of the 13 designed assays showed a clear separation between positive and negative droplets (FIG. 2A and FIG. 3). SYT10, EPHA3, PLEKHF1 and KBTBD4 had similar amplitude value of the negative droplet cluster (around 2000; FIG. 2A), and merging these assays into a control panel resulted in clear separation between positive and negative droplets (FIG. 2B). Combinations with other assays, e.g. ALDH1B1 and SAMSN1, which had a higher amplitude value of the negative droplet cluster (~2500-2800; FIG. 3), resulted in reduced separation (FIG. 2C). Thus, the

TABLE 1

| Gene | Accession Number | Chromosome | Amplicon Length | Sense Primer Sequence | Antisense Primer Sequence | Probe Sequence* |
|---|---|---|---|---|---|---|
| Control Candidate Assays - Approach A: Locus Shared by Members of a Gene Family ||||||||
| ALDOA | NM_000034 | 3, 10, 16 | 171 | SEQ ID NO: 22 | SEQ ID NO: 23 | SEQ ID NO: 24 |
| CYCS | NM_018947 | 6, 7, 8 | 152 | SEQ ID NO: 25 | SEQ ID NO: 26 | SEQ ID NO: 27 |
| Control Candidate Assays - Approach B: Combine Single Loci on Different Chromosomes ||||||||
| ALDH1B1 | NM_000692 | 9 | 108 | SEQ ID NO: 28 | SEQ ID NO: 29 | SEQ ID NO: 30 |
| ANKRD30A | NM_052997 | 10 | 101 | SEQ ID NO: 31 | SEQ ID NO: 32 | SEQ ID NO: 33 |
| EPHA3 | NM_005233 | 3 | 99 | SEQ ID NO: 4 | SEQ ID NO: 5 | SEQ ID NO: 6 |
| HAO2 | NM_016527 | 1 | 118 | SEQ ID NO: 34 | SEQ ID NO: 35 | SEQ ID NO: 36 |
| IGFBPL1 | NM_001007563 | 9 | 96 | SEQ ID NO: 37 | SEQ ID NO: 38 | SEQ ID NO: 39 |
| ITGAD | NM_005353 | 16 | 122 | SEQ ID NO: 40 | SEQ ID NO: 41 | SEQ ID NO: 42 |
| KBTBD4 | NM_001318724 | 19 | 86 | SEQ ID NO: 10 | SEQ ID NO: 11 | SEQ ID NO: 12 |
| MRPS5 | NM_001321995 | 2 | 78 | SEQ ID NO: 43 | SEQ ID NO: 44 | SEQ ID NO: 45 |
| NIPA2 | NM_001008860 | 15 | 106 | SEQ ID NO: 46 | SEQ ID NO: 47 | SEQ ID NO: 48 |
| PLEKHF1 | NM_024310 | 11 | 100 | SEQ ID NO: 7 | SEQ ID NO: 8 | SEQ ID NO: 9 |
| SAMSN1 | NM_022136 | 21 | 122 | SEQ ID NO: 49 | SEQ ID NO: 50 | SEQ ID NO: 51 |
| SYT10 | NM_198992 | 12 | 94 | SEQ ID NO: 1 | SEQ ID NO: 2 | SEQ ID NO: 3 |
| TTC5 | NM_138376 | 14 | 82 | SEQ ID NO: 52 | SEQ ID NO: 53 | SEQ ID NO: 54 |
| Previously-Suggested Control Genes ||||||||
| ACTB | Y00474 | 7 | 133 | SEQ ID NO: 55 | SEQ ID NO: 56 | SEQ ID NO: 57 |
| C-LESS-C1 | ** | 20 | 68 | SEQ ID NO: 58 | SEQ ID NO: 59 | SEQ ID NO: 60 |
| Target Genes ||||||||
| CDO1 | NM_001801 | 5 | 101 | SEQ ID NO: 61 | SEQ ID NO: 62 | SEQ ID NO: 63 |
| SEPT9 | NM_001113493 | 17 | 98 | SEQ ID NO: 64 | SEQ ID NO: 65 | SEQ ID NO: 66 |
| VIM | NM_003380 | 10 | 106 | SEQ ID NO: 67 | SEQ ID NO: 68 | SEQ ID NO: 69 |

All sequences are listed in 5' to 3' direction. All gene sequences are human. Primers were purchased from BioNordika Bergman, and probes from Life Technologies.
*All probes comprised a 3' minor groove binder and a 5' fluorophore. Probes for detection of control gene amplification were labelled with the fluorophore VIC; probes for detection of control gene amplification were labelled with the fluorophore 6-FAM.
** Obtained from the NCBI Build 36.2; chromosome 20, 19199387-19199455.

TABLE 2

| Cycling step | Temperature, ° C. | Time | Ramp rate | Number of cycles |
|---|---|---|---|---|
| Enzyme activation | 95 | 10 min | 2° C./sec | 1 |
| Denaturation | 94 | 30 sec | | 40 |
| Annealing/extension | 60 | 1 min | | 40 |
| Enzyme deactivation | 98 | 10 min | | 1 |
| Hold | 4 | Infinite | | 1 |

PCR thermal cycling conditions (using T100 Thermal Cycler, Bio-Rad). The conditions are those recommended by the manufacturer.

Results

The 4Plex Panel is the Best-Performing Control

Figure 4:
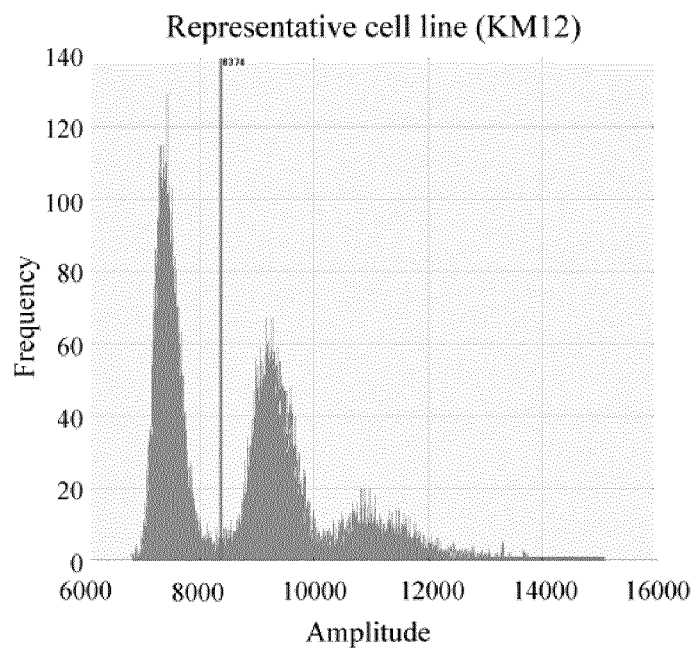
Figure 4:
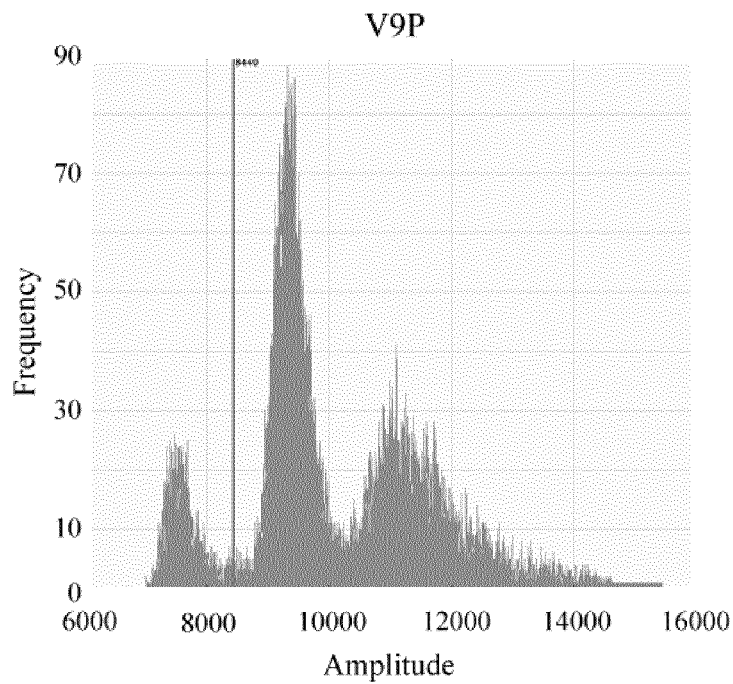

The gene family approach for designing an internal control (approach A) provided poor results (FIG. 1), and was discarded from further analyses. The ALDOA assay resulted in an IVD concentration of ~400 copies/μl (FIG. 1A), which was lower than expected based on the input amount and the number of targeted loci in the genome (n=3; Table 1). For CYCS, no positive droplet band was detected (FIG. 1B).

four-assay panel consisting of SYT10, EPHA3, PLEKHF1 and KBTBD4, termed the 4Plex, was identified as the best-performing control. Across all samples analysed the 4Plex provided a consistent amplification pattern, with V9P as an exception. This cell line displayed a shift in the droplet pattern, comprising a significant reduction of the negative droplet peak, and simultaneous increase of the positive droplet peak (FIG. 4).

The 4Plex has a Minor Impact on Amplification of the Target Gene

Figure 5:
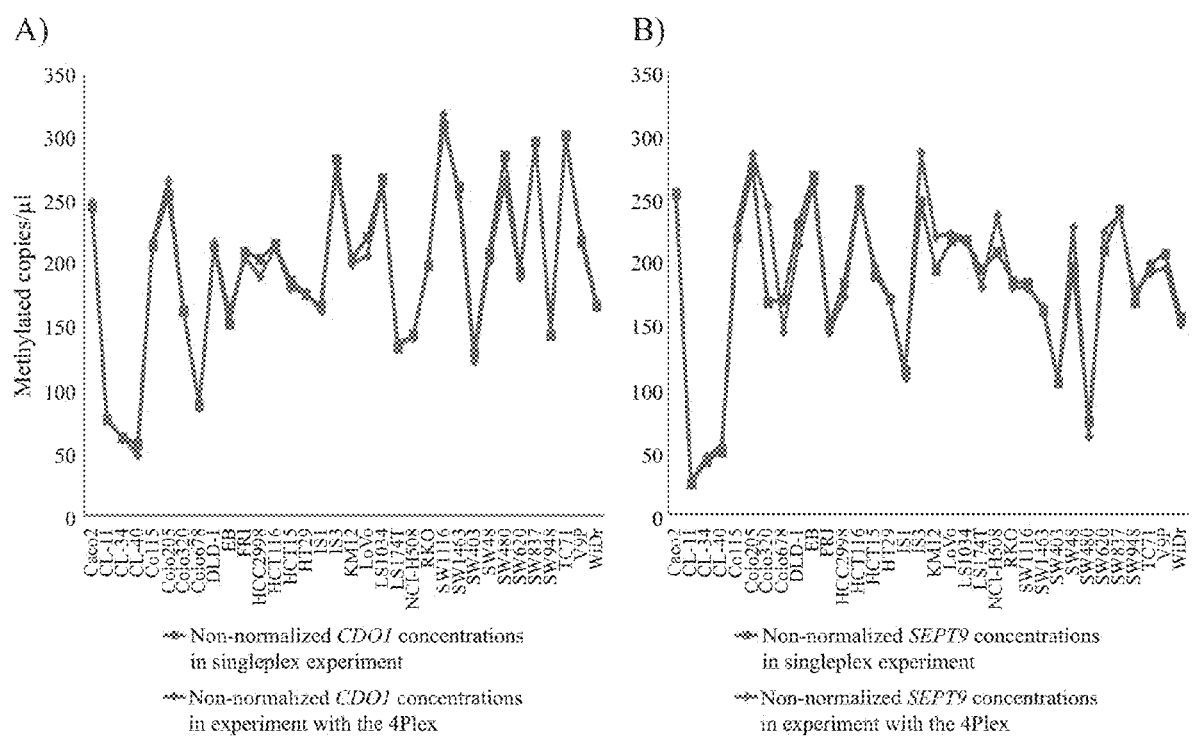
Figure 6:
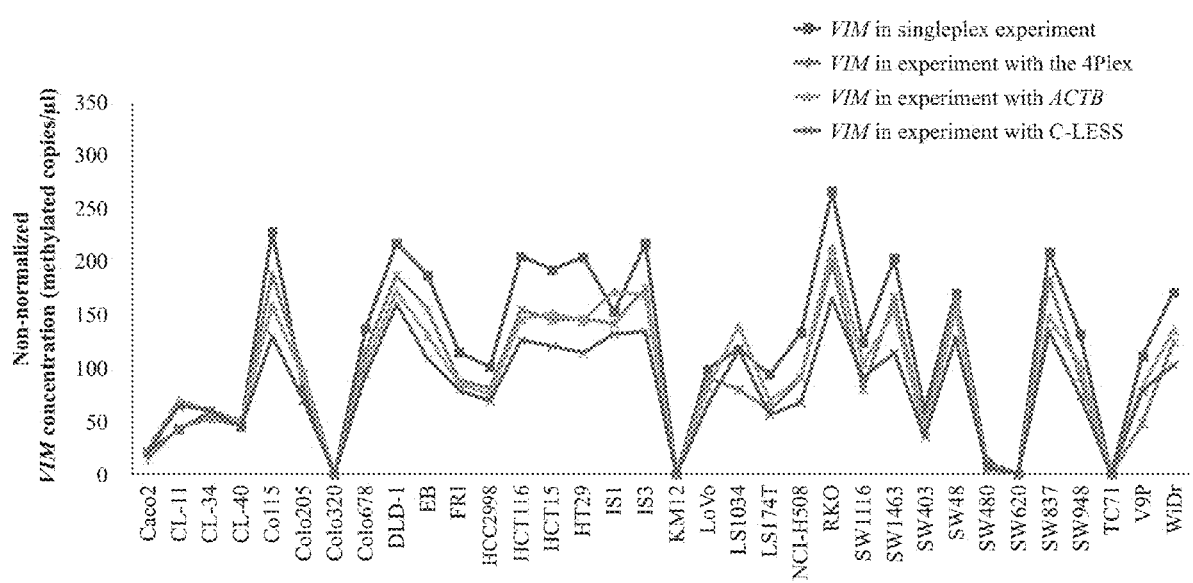

The assays comprised in the 4Plex control are labelled with VIC and run in the same reaction as the FAM-labelled methylation assay targeting a specific gene promoter. To evaluate whether the presence of the 4Plex had an impact on the amplification of the target gene, non-normalised target gene concentrations (methylated copies/μl) from experiments with and without the 4Plex control were compared. The resulting non-normalised concentrations were highly consistent for both CDO1 and SEPT9 (FIG. 5). For VIM, discrepancies between the concentrations resulting from the experiments with and without the 4Plex were observed (median absolute difference of 21%). However, this was comparable with resulting discrepancies from using the alternative controls ACTB (Eads, Supra) (median absolute difference of 23%) and C-LESS (Weisenberger, Supra) (median absolute difference of 38%; FIG. 6).

Figure 7:
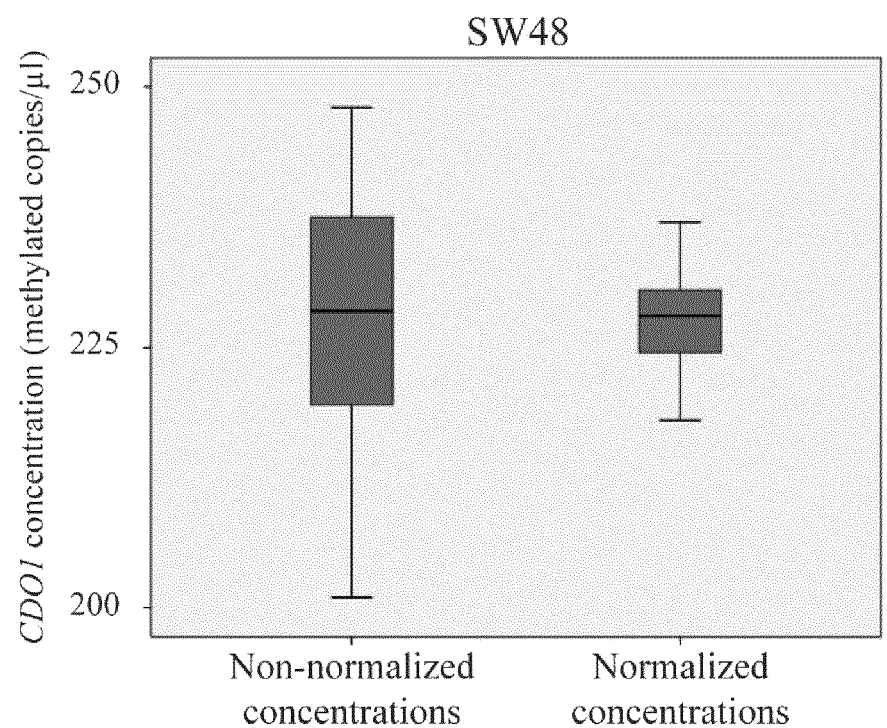
Figure 7:
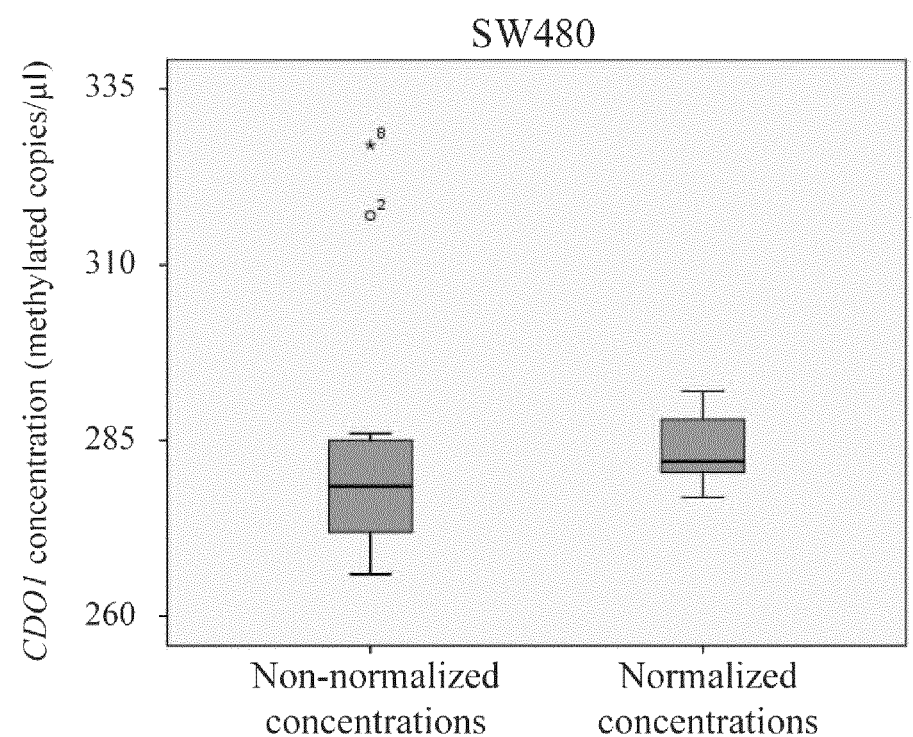
Figure 8:
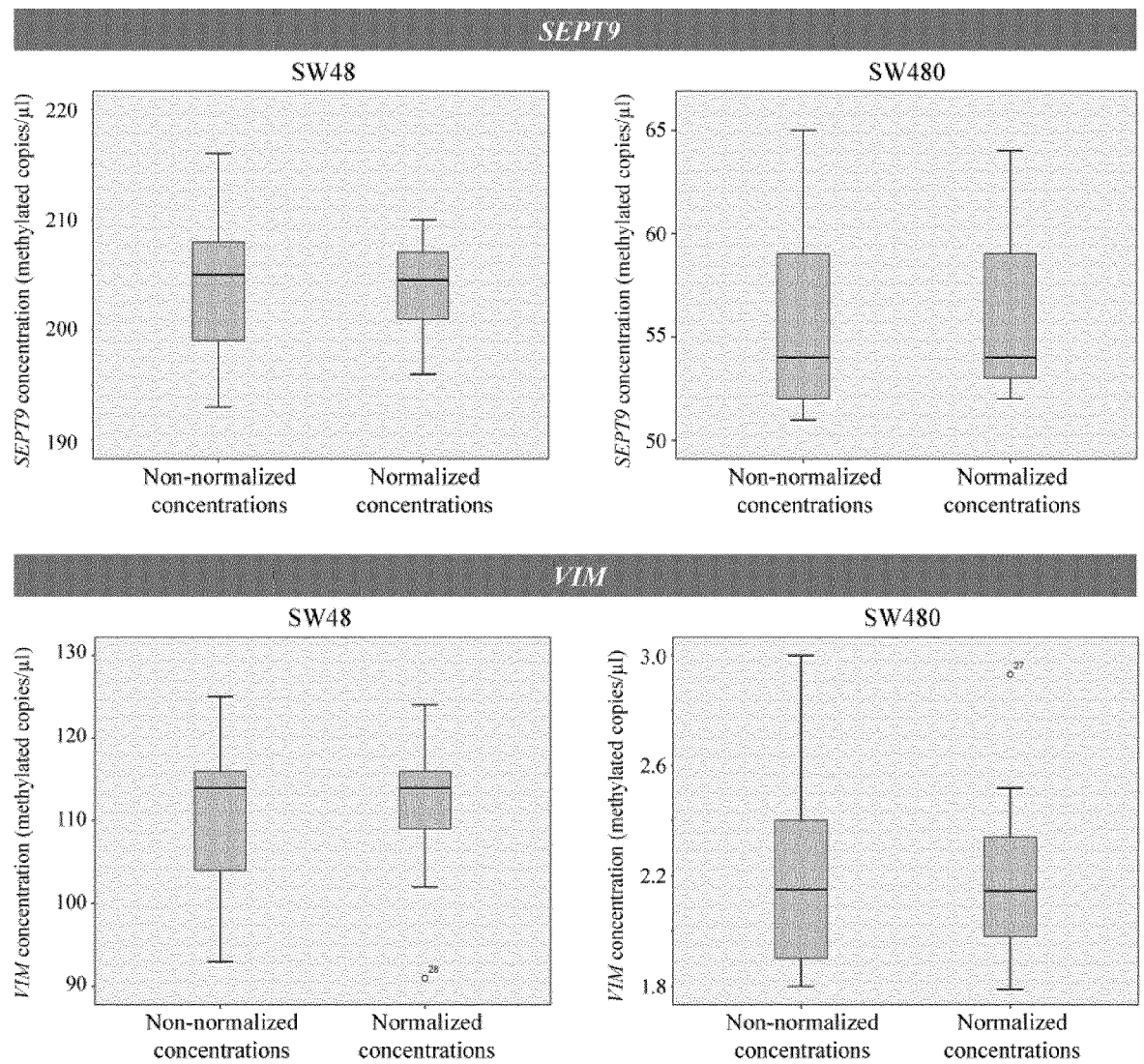

4Plex-Normalised Concentrations Show Less Variance than Non-Normalised Target Gene Concentrations Non-normalised and 4Plex-normalised concentrations of the target genes were compared among replicates of two different samples (SW48 and SW480), For both samples, normalised concentrations of CDO1 showed lower variance than the non-normalised concentrations (FIG. 7; 28.5 vs. 183 for SW48, and 20.3 vs. 356 for SW480). The same trend of reduced variability after normalisation was seen for SEPT9 and OM (FIG. 8).

Figure 9:
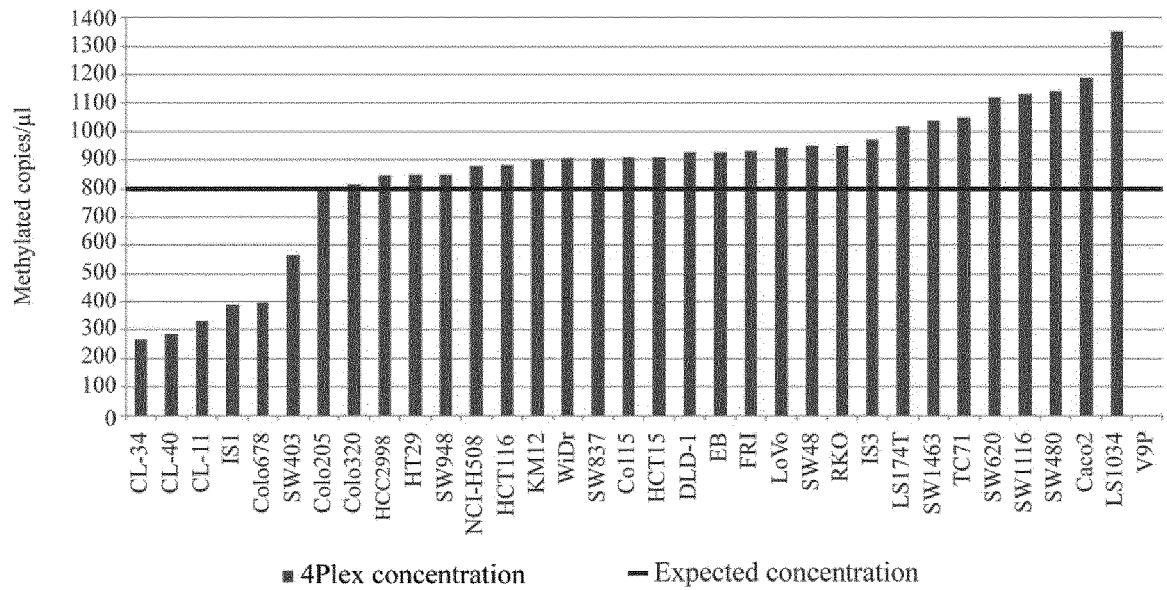
Figure 9:
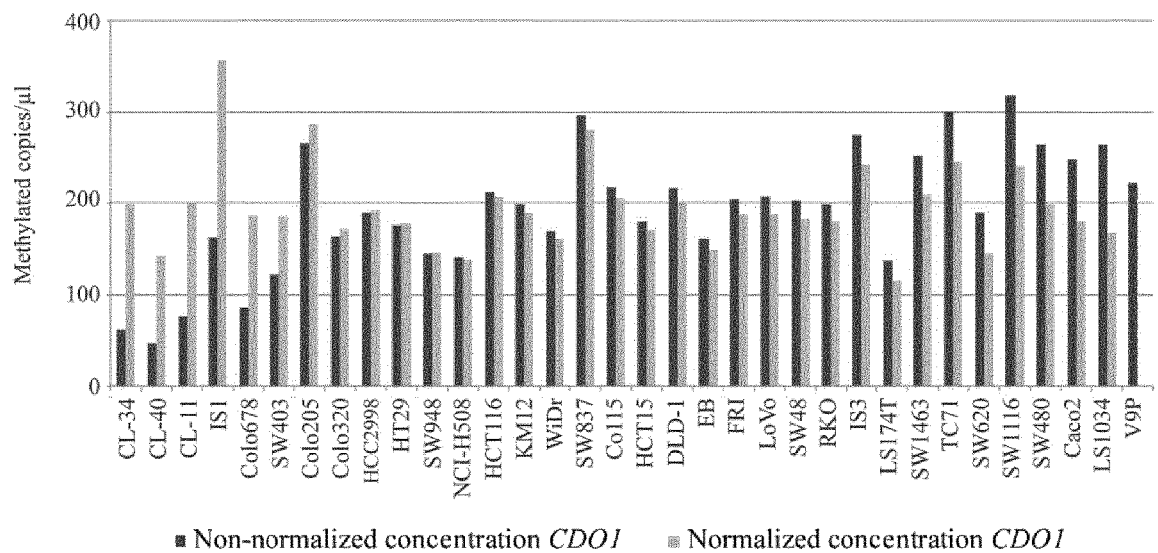
Figure 10:
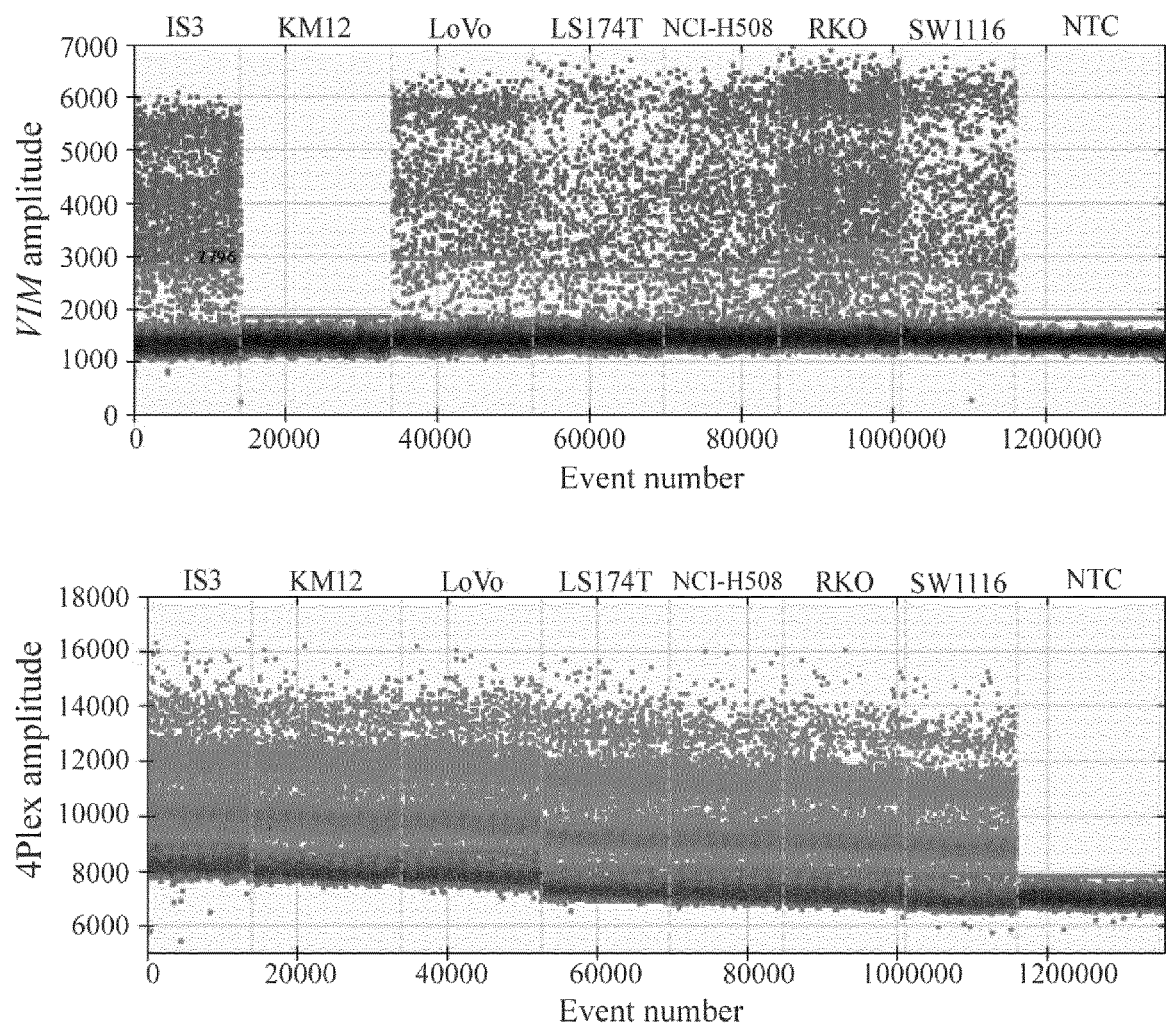
Figure 11:
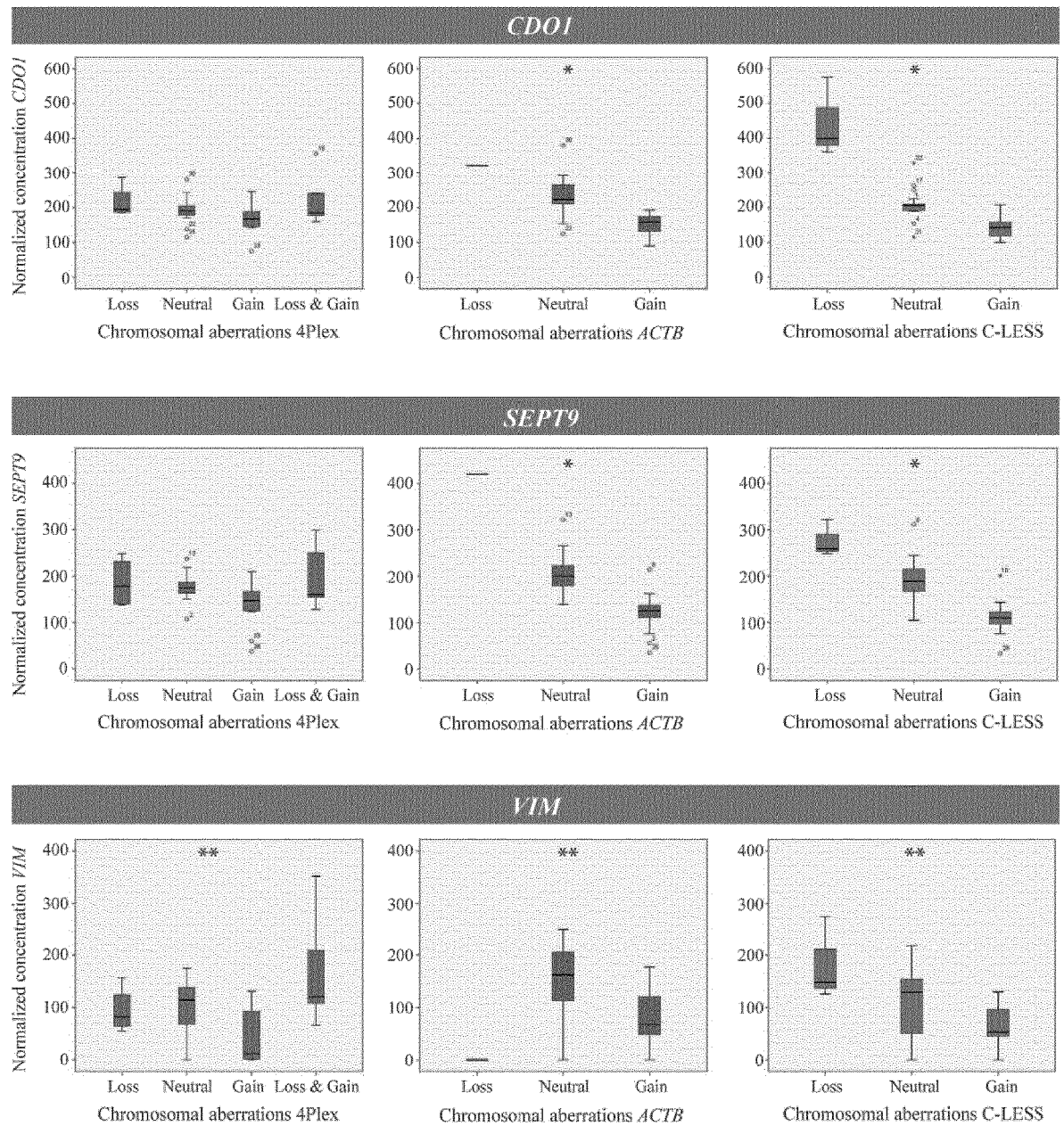

The 4Plex Corrects for Differences in Template Amounts, and Can Act as a Template-Loading Control The 4Plex revealed concentration differences across the cell line panel, despite use of the same theoretical input amount for all samples (based on the input amount in the bisulfite conversion; FIG. 9A), Moreover, comparing non-normalised and 4Plex-normalised concentrations of the target genes across the cell line panel, large differences were observed for the samples with the highest and lowest 4Plex concentrations (FIG. 9B). Finally, inclusion of the 4Plex discriminates true methylation-negative samples (e.g. KM12; FIG. 10), from potential false methylation-negative samples lacking template (NTC; FIG. 10), Normalisation by the 4Plex Diminishes the Effect of Chromosomal Aberrations To evaluate the potential impact of chromosomal aberrations on the 4Plex compared to the previously suggested single locus controls ACTB and C-LESS, the normalised concentrations of the target genes were compared in groups of colorectal cancer cell lines harboring no aberrations, gain, loss, or both gain and loss in the control loci (Table 3). As shown in FIG. 11, chromosomal aberrations significantly affected the ACTB-normalised concentrations (middle column) of CDO1, SEPT9 and VIM (P<0,001, P<0.001 and P=0.016, respectively) as well as the C-LESS-normalized concentrations of the same target genes (right-hand column; P<0.001, P<0.001 and P=0.012, respectively). In contrast, the 4Plex (left-hand column), was found to diminish the effect of chromosomal aberrations when analysing these three target genes (P=0.131, P=0.109, and P=0.011).

TABLE 3

Gene Copy Number States of ACTB, C-LESS and the 4Plex in the 34 Cell Lines

| Cell lines | Genomic loci | | | | | |
|---|---|---|---|---|---|---|
| | ACTB | C-LESS | EPHA3 | SYT10 | KBTBD4 | PLEKHF1 |
| Caco2 | 0 | 0 | 0 | 1 | 0 | 0 |
| CL-11 | 1 | 0 | 0 | 0 | 0 | 0 |
| CL-34 | 1 | 0 | 0 | 0 | 0 | 0 |
| CL-40 | 0 | 0 | 0 | 1 | 0 | 0 |
| Co115 | 0 | 0 | 0 | 0 | 0 | 0 |
| Colo205 | 0 | 1 | −1 | 0 | 0 | 0 |
| Colo320 | −1 | 0 | 0 | 1 | 0 | 0 |
| Colo678 | 1 | 0 | 0/−1* | 1 | 0 | 0 |
| DLD-1 | 0 | 0 | −1 | 0 | 0 | 0 |
| EB | 0 | 1 | 0 | 1 | 1 | 0 |
| FRI | 1 | −1 | 0 | 0 | 0 | −1 |
| HCC2998 | 1 | 0 | 0 | 0 | 0 | 0 |
| HCT116 | 0 | 0 | 0 | 0 | 0 | 0 |
| HCT15 | 0 | 0 | 0 | 0 | 0 | 0 |

TABLE 3-continued

Gene Copy Number States of ACTB, C-LESS and the 4Plex in the 34 Cell Lines

| Cell lines | Genomic loci | | | | | |
|---|---|---|---|---|---|---|
| | ACTB | C-LESS | EPHA3 | SYT10 | KBTBD4 | PLEKHF1 |
| HT29 | 0 | 0 | −1 | 1 | 1 | 1 |
| IS1 | 1 | 1 | −1 | 1 | 0 | −1 |
| IS3 | 1 | 0 | 0 | 0 | 0 | 0 |
| KM12 | 0 | 0 | 0 | 0 | 0 | 0 |
| LoVo | 1 | 0 | 0 | 0 | 0 | 0 |
| LS1034 | 0 | 1 | 0 | 1 | 1 | 0 |
| LS174T | 1 | 0 | 0 | 0 | 0 | 0 |
| NCI-H508 | 0 | 1 | 0 | 0 | 0 | 0 |
| RKO | 0 | 1 | 0 | 0 | 0 | 0 |
| SW1116 | 1 | −1 | −1 | 0 | 1 | −1 |
| SW1463 | 0 | 1 | 0 | 1 | 0 | 0 |
| SW403 | 1 | 1 | 0/−1* | 0 | 0 | −1 |
| SW48 | 1 | 0 | 0 | 0 | 0 | 0 |
| SW480 | 1 | 1 | 0 | 1 | 0 | 1 |
| SW620 | 1 | 1 | 0 | 1 | 1 | 0 |
| SW837 | 0 | −1 | 0 | 0 | 0 | 0 |
| SW948 | 1 | 1 | 0 | 0 | 1 | 0 |
| TC71 | 0 | 0 | 0 | 1 | 0 | 0 |
| VP9 | 1 | 1 | 0 | 0 | 0 | 1 |
| WiDr | 0 | 1 | −1 | 1 | 1 | 1 |

DNA copy number data from Affymetrix SNP6.0 arrays were preprocessed by the PennCNV protocol (adapted to Affymetrix arrays) and segmented using the R copynumber package. Gene copy number estimates of <−0.15 were called as loss, and >0.15 as gain, here given as gain = 1, neutral = 0 and loss = −1.
*Cell lines indicated to have two different, copy number states in one gene displayed a breakpoint in the gene, thereby the resulting different copy number state.

Discussion ddPCR technology allows highly sensitive quantification of nucleic acids, and has great potential for analysis of DNA methylation. In the present work, the inventors have developed a robust internal control for methylation-specific ddPCR, the 4Plex, which consists of four individual pericentromeric assays analysed in the same reaction as the target of interest. The inventors demonstrate that normalisation using the 4Plex standardises the results by increasing the precision of the target quantification. Such precision is especially important for the rapidly-evolving field of liquid biopsies, which has great potential for monitoring and detection of disease and emergence of drug resistance.

Two different strategies are used for robust quantification of methylated targets in ddPCR analyses. In line with standard mutation/SNP assays, primers binding equally efficiently to bisulfite converted DNA, independent of the DNA methylation status, can be paired with a probe mix of a first labelled probe binding exclusively to the amplicon obtained from amplification of the methylated DNA template and a second labelled probe (carrying a different and distinguishable label to the first probe) binding exclusively to the amplicon obtained from amplification of the unmethylated DNA template. With such a design the ratio between methylated and unmethylated DNA can be determined, reducing the normaliser to a control for minor variations, including pipetting inaccuracies etc. This represents a convenient design for absolute quantification, but can be challenging for DNA methylation analysis, where the number of CpGs in the target region of interest, e.g. in gene promoters, is often high. Presence of CpG sites in the primer binding sites may disturb the unbiasedness of the amplification. A commonly-used alternative, often seen in qPCR/MethyLight analyses (Eads et al., supra) is to design an assay amplifying only the methylated version of the target of interest, where both primers and probes contribute to the discrimination, Using this strategy, normalisation is essential. In traditional methylation analyses by MethyLight, the repetitive element ALU is frequently used as such an internal control, but is too abundant for ddPCR amplification and saturates the reaction. The 4Plex, on the other hand, amplifies multiple loci in the genome without reaching saturation.

There are several important reasons for using the 4Plex as an internal control in methylation-specific ddPCR. In addition to reducing the overall variability in methylation values and increasing the reproducibility, the 4Plex can adjust for unforeseen variations in the experimental pipeline. Although equal amounts of DNA, as measured by NanoDrop, were loaded into the bisulphite treatment and subsequent ddPCR reaction, the 4Plex revealed important DNA concentration differences across samples (FIG. 9A). Normalisation by the 4Plex prevented under- and overestimation of methylation levels (FIG. 9B). This is highly relevant for analyses of clinical material, where the DNA quality and integrity is typically variable.

As expected, the 4Plex served as a template-loading control that allowed distinction between true methylation-negative samples and template-negative samples (FIG. 10). However, as the 4Plex consists of four assays and has a considerably higher concentration than the target gene, it could also be used to establish a lower threshold for allowing scoring of samples. With a very low signal from the control, it is unlikely that the reaction contains enough templates to detect potential methylation. Such a lower loading-threshold, revealing samples that cannot be robustly determined, will reduce the number of false negatives.

Chromosomal aberrations are common in various diseases, and cancer in particular, and will affect the normalisation if present in the control locus. The importance of using a control panel that targets multiple loci for ddPCR DNA methylation analyses was recently also emphasized by Uehiro et al. (*Breast Cancer Res* 18(1): 129, 2016).The 4Plex presented here consists of four assays located on different chromosomes. When used as an internal control it reduced the effect of chromosomal aberrations on normalised methylation values of the target gene. In contrast, use of the single-locus controls ACTB and C-LESS caused significant deviations in methylation values (FIG. 11). An additional advantage of the 4Plex is that it only quantifies template that can be amplified by the targeted assays, i.e. bisulphite-converted DNA, in contrast to the C-LESS control that amplifies its target independent of bisulphite conversion status.

The 4Plex performed well across all samples analysed, with V9P as an exception (FIG. 4). This is most likely explained by the significant chromosomal amplification observed for the PLEKHF1 locus in this cell line. In contrast, a 'normal' droplet distribution pattern was seen across a series of more than 100 colorectal cancer tissues (data not shown), indicating that such pattern aberrations are rare. Furthermore, the 4Plex was successfully used by the inventors in recent analyses of non- to minimally-invasive material from bladder cancer- and cholangiocarcinoma patients, respectively (data not shown), underscoring that this control can be applied across cancer types.

Example 2—2Plex and 3Plex Alternatives

Having identified and validated the 4Plex as a control for digital PCR, the inventors investigated whether combinations of only 2 or 3 of the genes of the 4Plex are also useful controls (which combinations are known as 2Plexes and 3Plexes, respectively). Droplet digital PCR experiments were performed as described above in Example 1, using as a control the full 4Plex or a 2Plex or 3Plex combination. These gene combinations were used to normalise the concentration of the target gene CDO1 following its amplification from a panel of 10 different colorectal cancer cell lines.

Figure 12:
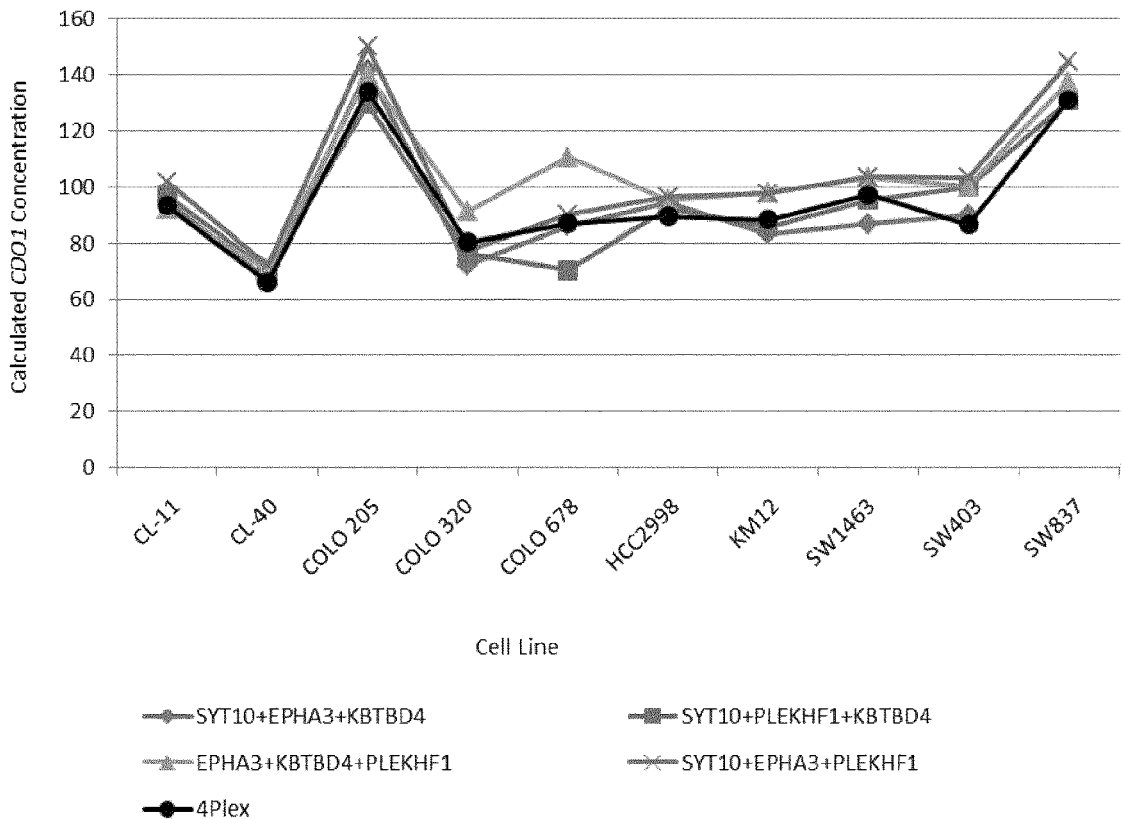
FIG. 12 shows the results of normalising the concentration of a target gene using 3Plex gene combinations. The figure shows the concentration of the target gene CDO1 (y-axis) across a colorectal cancer cell line panel (n=10; x-axis), as normalised using the 4Plex control or each combination of three of the genes in the 4Plex.

The results obtained with 3Plex combinations are presented in FIG. 12. All four possible 3Plex gene combinations were tested. As shown, in four of the cell lines (CL-11, CL40, HCC2998 and KM12) the 4 different 3Plex controls demonstrated comparable results to the 4Plex control (i.e. yielding an absolute difference in concentration between the 4Plex-normalised target gene concentration and the 3Plex-normalised target gene concentration ≤10, determined as methylated copies/µl). In the other 6 cell lines one or more of the 3Plex combinations yielded normalised results which deviate from the 4Plex control results.

The largest deviations are seen for cancer cell line COLO 678, which harbours a chromosomal loss at the EPHA3 locus and a gain at the SYT10 locus, explaining why the SYT10/PLEKHF1/KBTBD combination (one net gain) demonstrates a lower normalised target gene concentration than expected, whereas the EPHA3/KBTBD5/PLEKHF1 (one net loss) demonstrates a higher normalised target gene concentration compared with using the 4Plex control (which harbours one gain and one loss and thus a net change of zero).

The results indicate that the 3Plex combinations can be useful for normalisation of amplification results, though they do not provide the same level of accuracy as the 4Plex control. The four different 3Plex combinations have comparable performances across the cancer cell line panel (yielding results which deviate from the 4Plex results in 1 to 3 of the tested cell lines), underscoring that none of the 3Plex combinations is superior to the others.

Figure 13:
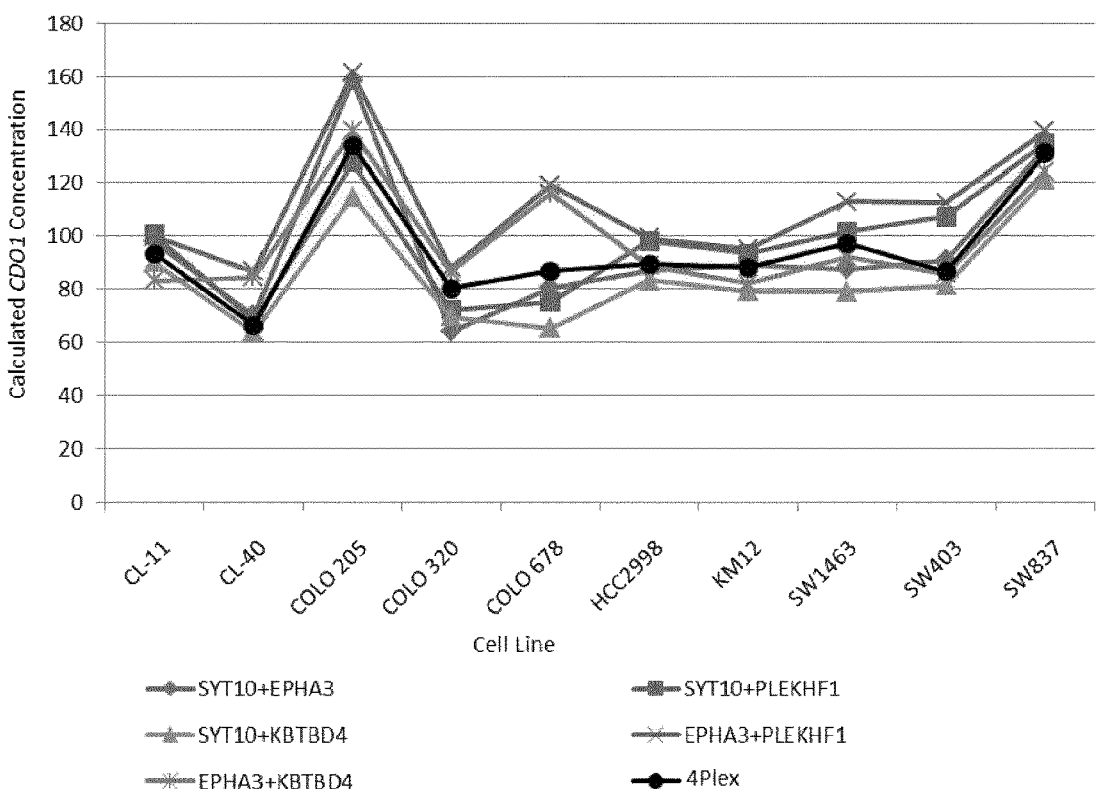
FIG. 13 shows the results of normalising the concentration of a target gene using 2Plex gene combinations. The figure shows the concentration of the target gene CDO1 (y-axis) across a colorectal cancer cell line panel (n=10; x-axis), as normalised using the 4Plex control or various combinations of two of the genes in the 4Plex.

The results obtained with 2Plex combinations are shown in FIG. 13. Five 2Plex combinations were tested (the combination of PLEKHF1 and KBTBD4 was not). As shown, in three of the cell lines (HCC2998, KM12 and SW837) the 5 tested 2Plex controls demonstrated comparable results to the 4Plex control (i.e. yielding an absolute difference in concentration between the 4Plex-normalised target gene concentration and the 2Plex-normalised target gene concentration ≤10). In the other 7 cell lines one or more of the 2Plex combinations yielded normalised results which deviate from the 4Plex control results. Again, and for the same reasons as above, the largest deviations are seen for cancer cell line COLO 678.

The results indicate that the 2Plex combinations can also be useful for normalisation of amplification results, though they do not provide the same level of accuracy as the 4Plex control (or of the 3Plex controls). The five tested 2Plex combinations have comparable performances across the cancer cell line panel (yielding results which deviate from the 4Plex results in 2 to 5 of the tested cell lines), underscoring that none of the 2Plex combinations is superior to the others.

The invention claimed is:

1. A method of quantification of a target nucleic acid, wherein at least any two of the genes SYT10, EPHA3, PLEKHF1 and KBTBD4 are used as control genes, said method comprising:
(i) amplifying the target nucleic acid, or a target region thereof, to yield a target amplicon, wherein the amplification is performed using a quantitative amplification method which allows absolute quantification and which uses primers;
(ii) amplifying a target region of at least two of the control genes SYT10, EPHA3, PLEKHFI and KBTBD4, to yield a control gene amplicon for each of the at least two control genes, wherein the amplification is performed using a quantitative amplification method which allows absolute quantification and which uses primers, wherein no more than one target region of any one of the control genes is amplified;
(iii) normalising the results of the target amplification of (i) using the results of the control amplification of the target regions of the at least two control genes of (ii); and
(iv) based on (iii), determining a value for the amount of the target nucleic acid.

2. The method of claim 1, wherein in (i) and (ii) the quantitative amplification methods which allow absolute quantification and which use primers are the same quantitative amplification method; and/or
wherein the quantitative amplification method comprises a PCR reaction.

3. The method of claim 1, wherein in (i):
(A) one of the primers used to amplify the target nucleic acid, or the target region thereof, comprises a 5' tail which is not complementary to the target nucleic acid or the target region thereof, and the amplification is performed in the presence of a fluorescent probe which specifically binds the 5' tail; or
(B) amplification of the target nucleic acid, or the target region thereof, is performed in the presence of a fluorescent probe which specifically binds the target amplicon; and/or wherein in (ii):
(A) one of the primers used to amplify the target region of one or more of the at least two control genes comprises a 5' tail which is not complementary to the target region, and the amplification is performed in the presence of a fluorescent probe which specifically binds the 5' tail; and/or
(B) amplification of one or more of the target regions of the at least two control genes is performed in the presence of a fluorescent probe which specifically binds the control gene amplicon.

4. The method of claim 1, wherein the target nucleic acid is:
a target gene or a target gene promoter;
a biomarker;
human DNA; and/or
comprised within a clinical or veterinary sample.

5. The method of claim 1, wherein the target nucleic acid is a methylated DNA target, and the method comprises quantifying the amount of methylated target DNA in a sample comprising the target DNA.

6. The method of claim 5, wherein the method comprises:
(a) subjecting a sample comprising the target DNA to bisulphite conversion;
(b) amplifying the target DNA, or a target region thereof, to yield a target amplicon, wherein the amplification is performed using a quantitative amplification method which allows absolute quantification and which uses primers;
(c) amplifying a target region of at least two of the control genes SYT10, EPHA3, PLEKHFI and KBTBD4 to yield a control gene amplicon for each of the at least two control genes, wherein the amplification is performed using the same quantitative amplification method as used in (b), and wherein no more than one target region of any one of the control genes is amplified; and
(d) normalising the results of the target amplification of (b) using the results of the control amplification of the target regions of the at least two control genes of (c); and
(e) based on (d), determining a value for the amount of the methylated target DNA.

7. The method of claim 6, wherein the amplification of (b) is methylation-specific PCR, and is performed using methylation-specific primers, and wherein the amplification of (c) is performed using primers which bind the control gene at sites which do not contain any CpG dinucleotides.

8. The method of claim 1, wherein at least any 3 of the genes SYT10, EPHA3, PLEKHFI and KBTBD4 are used as controls, wherein in (iii) normalisation of the results of the target amplification of (i) is performed using the results of the control amplification of the target regions of the at least three control genes of (ii).

9. The method of claim 1, wherein each of the genes SYT10, EPHA3, PLEKHFI and KBTBD4 are used as controls, wherein in (iii) normalisation of the results of the target amplification of (i) is performed using the results of the control amplification of the target regions of each of the control genes of (ii).

10. The method of claim 7, wherein in (b) the methylation-specific PCR amplification of the target DNA, or a target region thereof, is performed in the presence of a fluorescent probe which specifically binds the target amplicon, optionally wherein binding of the fluorescent probe to the target amplicon is methylation specific;
and wherein in (c) the amplification of the single target regions of each of the control genes is performed in the presence of a fluorescent probe which specifically binds the control gene amplicon at a site which does not contain any CpG dinucleotides.

11. The method of claim 10, wherein the methylation-specific PCR amplification of the target DNA of (b) and the PCR amplification of the target regions of the control genes of (c) are performed simultaneously in the same reaction mixture.

12. The method of claim 1, wherein the quantitative amplification method used in (i) and (ii) is digital PCR or absolute quantification qPCR.

13. The method of claim 12, wherein the digital PCR is droplet digital PCR.

14. The method of claim 1, wherein:
(i) SYT10 is used as a control gene and a target region within exon 3 of SYT10 is amplified; and/or
(ii) EPHA3 is used as a control gene and a target region within exon 3 of EPHA3 is amplified; and/or
(iii) PLEKHF1 is used as a control gene and a target region within exon 2 of PLEKHFI is amplified; and/or
(iv) KBTBD4 is used as a control gene and a target region within exon 4 of KBTBD4 is amplified.

15. The method of claim 14, wherein the target region of SYT10 has the sequence set forth in SEQ ID NO: 13; and/or
the target region of EPHA3 has the sequence set forth in SEQ ID NO: 14; and/or
the target region of PLEKHFI has the sequence set forth in SEQ ID NO: 15; and/or
the target region of KBTBD4 has the sequence set forth in SEQ ID NO: 16.

16. The method of claim 7, wherein said method comprises:
(a) subjecting a sample comprising the target DNA to bisulphite conversion;
(b) amplifying the target DNA, or a target region thereof, to yield a target amplicon, wherein the amplification is performed by droplet digital PCR using methylation-specific primers and in the presence of a fluorescent probe, wherein:
(i) the fluorescent probe specifically binds the target amplicon; or
(ii) one of the primers used to amplify the target DNA, or target region thereof, comprises a 5' tail to which the fluorescent probe specifically binds;
(c) amplifying a target region of each of the control genes SYT10, EPHA3, PLEKHFI and KBTBD4 to yield a control gene amplicon for each of the control genes, wherein the amplification is performed by droplet digital PCR using primers which bind the control genes at sites which do not contain any CpG dinucleotides, wherein no more than one target region of any one of the control genes is amplified, wherein the PCR amplification of the target regions of the control genes is performed simultaneously in the same reaction mixture as the methylation-specific PCR amplification of the target DNA of (b), and wherein the amplification of the single target regions of each of the control genes is performed in the presence of a fluorescent probe, wherein:
(I) each fluorescent probe specifically binds one of the control gene amplicons at a site which does not contain any CpG dinucleotides; or
(II) one of the primers used to amplify the target region of each control gene comprises a 5' tail to which one of the fluorescent probes specifically binds; or
(III) the probes are a mixture of probes as defined in (I) and probes as defined in (II);
(d) normalising the results of the target amplification of (b) using the results of the control amplification of the target regions of the control genes of (c); and
(e) based on (d), determining a value for the amount of the methylated target DNA.

17. The method of claim 4, wherein the clinical or veterinary sample is a blood sample, a plasma sample, a saliva sample, a urine sample or a biopsy.

18. A kit comprising two or more primer sets suitable for use in PCR to amplify a target region within a target gene to generate an amplicon, said two or more primer sets selected from primer sets comprising:
(i) a first primer and a second primer which bind within SYT10;
(ii) a first primer and a second primer which bind within EPHA3;
(iii) a first primer and a second primer which bind within PLEKHF1; and
(iv) a first primer and a second primer which bind within KBTBD4;
wherein the first primers and the second primers of the two or more primer sets each bind a site within the target gene which does not contain any CpG dinucleotides; and each primer set further comprises a fluorescent probe which binds the amplicon generated by PCR using the first primer and second primer of the primer set, wherein the fluorescent probe binds the amplicon at a site which does not contain any CpG dinucleotides.

19. The kit of claim 18, wherein when the kit comprises the primer set of part:
(i), the first primer and the second primer each bind within exon 3 of SYT10;
(ii), the first primer and the second primer each bind within exon 3 of EPHA3;
(iii), the first primer and the second primer each bind within exon 2 of PLEKHF1; or
(iv), the first primer and the second primer each bind within exon 4 of KBTBD4.

20. The kit of claim 19, wherein when the kit comprises the primer set of part:
(i), the primer set is suitable for use in PCR to amplify a target region with the sequence set forth in SEQ ID NO: 13;
(ii), the primer set is suitable for use in PCR to amplify a target region with the sequence set forth in SEQ ID NO: 14;
(iii), the primer set is suitable for use in PCR to amplify a target region with the sequence set forth in SEQ ID NO: 15; or
(iv), the primer set is suitable for use in PCR to amplify a target region with the sequence set forth in SEQ ID NO: 16.

21. The kit of claim 18, wherein the kit comprises the primer pairs of parts (i), (ii), (iii) and (iv).

* * * * *